United States Patent
Takahara et al.

(10) Patent No.: US 10,761,044 B2
(45) Date of Patent: Sep. 1, 2020

(54) SENSOR AND CONCENTRATION MEASUREMENT METHOD

(71) Applicant: PHC Holdings Corporation, Tokyo (JP)

(72) Inventors: Yoshifumi Takahara, Ehime (JP); Takahiro Nakaminami, Ehime (JP); Shin Ikeda, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 165 days.

(21) Appl. No.: 14/936,964

(22) Filed: Nov. 10, 2015

(65) Prior Publication Data

US 2016/0061764 A1    Mar. 3, 2016

Related U.S. Application Data

(63) Continuation of application No. 13/392,630, filed as application No. PCT/JP2010/005341 on Aug. 30, 2010, now Pat. No. 9,212,380.

(30) Foreign Application Priority Data

Aug. 31, 2009 (JP) .................................. 2009-201116

(51) Int. Cl.
*G01N 27/327* (2006.01)
*C12Q 1/00* (2006.01)
(Continued)

(52) U.S. Cl.
CPC ......... *G01N 27/3272* (2013.01); *C12Q 1/006* (2013.01); *C12Q 1/32* (2013.01); *G01N 21/8483* (2013.01)

(58) Field of Classification Search
CPC .. G01N 27/327–3274; C12Q 1/00–006; C12Q 1/26–32
See application file for complete search history.

(56) References Cited

U.S. PATENT DOCUMENTS 5,288,636 A * 2/1994 Pollmann ............... C12Q 1/004
                                                             204/403.14
6,212,417 B1   4/2001 Ikeda et al.
(Continued)

FOREIGN PATENT DOCUMENTS

| CN | 1250161 | 4/2000 |
| CN | 1110700 | 6/2003 |

(Continued)

OTHER PUBLICATIONS

L. F. Fieser "The Reduction Potential of Various Phenanthrenequinones" Journal of the American Chemical Society, vol. 51, No. 10, Oct. 1929, p. 3101-3111. (Year: 1929).*

(Continued)

*Primary Examiner* — J. Christopher Ball
(74) *Attorney, Agent, or Firm* — Wenderoth, Lind & Ponack, L.L.P.

(57) ABSTRACT

A reagent layer of a sensor contains as a mediator a quinone compound having a hydrophilic functional group, phenanthrenequinone, and/or a phenanthrenequinone derivative. The quinone compound has a lower redox potential than a conventional mediator, so interfering substances have less effect on detection results with this sensor.

5 Claims, 18 Drawing Sheets

(51) Int. Cl.
*C12Q 1/32* (2006.01)
*G01N 21/84* (2006.01)

(56) References Cited

U.S. PATENT DOCUMENTS

| | | |
|---|---|---|
| 6,214,612 B1 | 4/2001 | Yamamoto et al. |
| 6,258,254 B1 | 7/2001 | Miyamoto et al. |
| 6,736,957 B1 | 5/2004 | Forrow et al. |
| 6,773,564 B1 | 8/2004 | Yugawa et al. |
| 6,875,327 B1 | 4/2005 | Miyazaki et al. |
| 2002/0027072 A1 | 3/2002 | Cui et al. |
| 2003/0146110 A1 | 8/2003 | Karinka et al. |
| 2004/0178066 A1 | 9/2004 | Miyazaki et al. |
| 2004/0178067 A1 | 9/2004 | Miyazaki et al. |
| 2004/0197935 A1 | 10/2004 | Forrow et al. |
| 2004/0234945 A1 | 11/2004 | Horn et al. |
| 2007/0289881 A1 | 12/2007 | Forrow et al. |
| 2008/0213808 A1* | 9/2008 | Knappe .............. C12Q 1/32 435/11 |
| 2008/0305469 A1 | 12/2008 | Horn et al. |
| 2009/0065356 A1 | 3/2009 | Nakayama et al. |
| 2009/0090624 A1 | 4/2009 | Forrow et al. |
| 2009/0090625 A1 | 4/2009 | Forrow et al. |
| 2009/0152111 A1 | 6/2009 | Miyazaki et al. |
| 2009/0166223 A1 | 7/2009 | Forrow et al. |
| 2010/0243443 A1 | 9/2010 | Miyazaki et al. |
| 2011/0117269 A1 | 5/2011 | Miyazaki et al. |
| 2011/0147234 A1 | 6/2011 | Miyazaki et al. |
| 2011/0174613 A1 | 7/2011 | Miyazaki et al. |
| 2011/0272296 A1 | 11/2011 | Miyazaki et al. |
| 2011/0278167 A1 | 11/2011 | Miyazaki et al. |

FOREIGN PATENT DOCUMENTS

| | | |
|---|---|---|
| CN | 101427128 | 5/2009 |
| EP | 0 136 362 | 4/1985 |
| EP | 0 794 429 A1 | 9/1997 |
| EP | 0 894 869 A1 | 2/1999 |
| EP | 0 984 069 | 3/2000 |
| JP | 3-202764 | 9/1991 |
| JP | 9-297121 | 11/1997 |
| JP | 2000-171428 | 6/2000 |
| JP | 2001-305095 | 10/2001 |
| JP | 2001-520367 | 10/2001 |
| JP | 2002-90331 | 3/2002 |
| JP | 2004-258021 | 9/2004 |
| JP | 2010-237145 | 10/2010 |
| WO | 2007/123179 | 11/2007 |

OTHER PUBLICATIONS

International Search Report dated Dec. 7, 2010 in International (PCT) Application No. PCT/JP2010/005341.
Yu. Yu. Kulis et al., "Enzymatic Oxidation of Glucose on Modified Electrodes", Biokhimiya, vol. 46, No. 10, 1981, pp. 1780-1786 along with English translation.
Chinese Office Action dated Aug. 15, 2013 in corresponding Chinese Application No. 201080034694.0.
J.J. Kulys et al., "Oxidation of Glucose Oxidase from Penicillium Vitale by One- and Two-electron Acceptors", Biochimica et Biophysica Acta(BBA)—Protein Structure and Molecular Enzymology, vol. 744, the 1st issue, p. 57-63, Apr. 14, 1983.
Extended European Search Report issued in corresponding Application No. 10811541.1 and dated Jul. 10, 2014.
I. Lapenaite et al., "Some quinone derivatives as redox mediators for PQQ-dependent glucose dehydrogenase", Biologija, No. 1, Jan. 1, 2004, pp. 20-22, XP055126365.
Office Action dated Mar. 7, 2017 in corresponding European Patent Application No. 10811541.1.
Fieser, Louis F., "The Reduction Potentials of Various Phenanthrenequinones", Journal of the American Chemical Society, vol. 51, No. 10, pp. 3101-3111 (1929).
Extended European Search Report dated Jul. 30, 2018 in European Application No. 18151485.2.

* cited by examiner

SENSOR AND CONCENTRATION MEASUREMENT METHOD

TECHNICAL FIELD

The present invention relates to a sensor detecting or quantifying a target substance in a liquid sample, and to a method for measuring the concentration of a target substance.

BACKGROUND

A sensor for detecting a target substance in a biological sample has been proposed in the past. With a blood glucose sensor, which is an example of a sensor, the biological sample is blood, and the target substance is glucose.

Most of the blood glucose sensors that have been proposed are electrochemical blood glucose sensors. An electrochemical blood glucose sensor comprises an enzyme and a mediator. This enzyme oxidizes glucose by specifically reacting with the glucose in blood. The mediator accepts electrons generated by oxidation. The mediator that has accepted these electrons is electrochemically oxidized by electrodes, for example. The glucose concentration in the blood, that is, the blood glucose level, is easily detected from the amount of current obtained by this oxidation.

In the past, potassium ferricyanide has usually been used as the mediator in the above-mentioned type of electrochemical blood glucose sensors (see Patent Literature 1, for example). Potassium ferricyanide is chemically stable in a dry state at room temperature, and is also low in cost. Furthermore, potassium ferricyanide has high solubility in samples whose solvent is water, such as blood. Thus, potassium ferricyanide is particularly favorable with certain sensors (those in which an enzyme and a mediator are actively dissolved in blood during blood glucose detection).

The ferricyanide ions contained in potassium ferricyanide dissolve quickly in blood, accept electrons from the enzyme that has reacted with glucose, and become ferrocyanide ions. These ions are electrochemically oxidized by electrodes, and produce current corresponding to the blood glucose level.

However, with a blood glucose sensor in which potassium ferricyanide is used as a mediator, a problem was that measurement error was caused by other substances present in the blood. This measurement error occurs as follows. Ascorbic acid (vitamin C) and other such substances are present along with glucose in blood. Ascorbic acid is oxidized by the electrodes in the blood glucose sensor along with the ferrocyanide ions. As a result, current originating in ascorbic acid is superimposed with current originating in the blood glucose level, and the resulting current value is detected as current expressing the blood glucose level. This is what causes measurement error.

This measurement error occurs because the potential of the electrodes needed to oxidize the ferrocyanide ions is significantly higher (positive) than the potential for oxidizing ascorbic acid. Specifically, the oxidation potential of the ferrocyanide ions themselves (approximately 160 mV vs. Ag|AgCl) is far higher than that of ascorbic acid (approximately −140 mV vs. Ag|AgCl), so a large measurement error results.

CITATION LIST

Patent Literature

Patent Literature 1: Japanese Laid-Open Patent Application 2001-305095

Patent Literature 2: Japanese Unexamined Patent Application Publication (Translation of PCT Application) No 2001-520367

SUMMARY

In light of the above-mentioned problem of measurement error encountered with the prior art discussed above, it is an object of the present invention to provide a sensor and a concentration measurement method that are less susceptible to the effect of interfering substances.

The sensor of the first invention is a sensor for detecting or quantifying a target substance contained in a liquid sample, comprising a PQQ-dependent or FAD-dependent enzyme, a quinone compound having a hydrophilic functional group, and at least a pair of electrodes. The PQQ-dependent or FAD-dependent enzyme dehydrogenates or oxidizes the target substance by coming into contact with the liquid sample. The quinone compound accepts electrons from the enzyme. When voltage is applied between the pair of electrodes, one of the electrodes accepts electrons from the quinone compound.

The sensor of the second invention is a sensor for detecting or quantifying a target substance contained in a liquid sample, comprising a quinone compound having a hydrophilic functional group, an oxidase, and at least a pair of electrodes. The oxidase oxidizes the target substance by coming into contact with the liquid sample. The quinone compound accepts electrons from the oxidase. When voltage is applied between the pair of electrodes, one of the electrodes accepts electrons from the quinone compound.

The sensor of the third invention is a sensor for detecting or quantifying a target substance contained in a liquid sample, comprising a quinone compound having a hydrophilic functional group, a dehydrogenase, and at least a pair of electrodes. The dehydrogenase dehydrogenates the target substance by coming into contact with the liquid sample. The quinone compound accepts electrons from the dehydrogenase. When voltage is applied between the pair of electrodes, one of the electrodes accepts electrons from the quinone compound.

With the first, second, and third inventions, the sensor comprises a quinone compound having a hydrophilic functional group. A quinone compound having a hydrophilic functional group is expected to have better solubility in water than a quinone compound that has no hydrophilic functional group. If a quinone compound has better solubility in water, the quinone compound will have more opportunities to collide with the enzyme molecules and the target substance dissolved in a liquid sample. As a result, it is anticipated that there will be an increase in response current and measurement will take less time.

Furthermore, a quinone compound having a hydrophilic functional group is expected to have lower volatility than a quinone compound that has no hydrophilic functional group.

Furthermore, if the sensor comprises a quinone compound having a hydrophilic functional group, it is anticipated that there will be an increase in the amount of quinone compound had by the sensor as compared to when the sensor comprises a quinone compound that has no hydrophilic functional group.

The sensor of the fourth invention is a sensor for detecting or quantifying a target substance contained in a liquid sample, comprising phenanthrenequinone and/or a derivative thereof as a mediator, an enzyme, and at least a pair of electrodes. The enzyme dehydrogenates or oxidizes the target substance by coming into contact with the liquid sample. The phenanthrenequinone and/or derivative thereof accepts electrons from the enzyme. When voltage is applied between the pair of electrodes, one of the electrodes accepts electrons from the phenanthrenequinone and/or derivative thereof.

Because the sensor comprises phenanthrenequinone or a derivative thereof as a mediator, the measurement result is less apt to be affected by readily oxidizable measurement interfering substances in the liquid sample. Thus, with the invention of the fourth invention, it is anticipated that the target substance can be detected at a higher reliability.

The method of the fifth invention is a method for measuring the concentration of a target substance contained in a liquid sample, comprising the steps of:

(a) bringing into contact the liquid sample, a PQQ-dependent or FAD-dependent enzyme, and the quinone compound having a hydrophilic functional group;

(b) dehydrogenating or oxidizing the target substance contained in the liquid sample with the PQQ-dependent or FAD-dependent enzyme;

(c) accepting electrons from the PQQ-dependent or FAD-dependent enzyme with the quinone compound;

(d) applying voltage to a pair of electrodes in contact with the liquid sample;

(e) oxidizing the quinone compound that has accepted electrons in (c) above with one of the pair of electrodes;

(f) measuring the current flowing between the pair of electrodes; and (g) calculating the concentration of the target substance on the basis of the current.

The method of the sixth invention is a method for measuring the concentration of a target substance contained in a liquid sample, comprising the steps of:

(a) bringing into contact the liquid sample, a quinone compound having a hydrophilic functional group, and an oxidase whose substrate is the target substance and which donates electrons to the quinone compound;

(b) detecting the current produced by (a) above; and (c) calculating the concentration of the target substance on the basis of the detection result of (b) above.

The method of the seventh invention is a method for measuring the concentration of a target substance contained in a liquid sample, comprising the steps of:

(a) bringing into contact the liquid sample, a quinone compound having a hydrophilic functional group, and a dehydrogenase whose substrate is the target substance and which donates electrons to the quinone compound;

(b) detecting the current produced by (a) above; and (c) calculating the concentration of the target substance on the basis of the detection result of (b) above.

A quinone compound having a hydrophilic functional group is expected to have better solubility in water than a quinone compound that has no hydrophilic functional group. Thus, a quinone compound having a hydrophilic functional group will have more opportunities to collide with the enzyme molecules and the target substance dissolved in a liquid sample. As a result, it is anticipated that there will be an increase in response current and measurement will take less time with the fifth to seventh inventions.

The method of the eighth invention is a method for measuring the concentration of a target substance contained in a liquid sample, comprising the steps of:

(a) bringing into contact the liquid sample, phenanthrenequinone and/or a derivative thereof, and an enzyme whose substrate is the target substance and which donates electrons to the phenanthrenequinone and/or a derivative thereof;

(b) detecting the current produced by (a) above; and (c) calculating the concentration of the target substance on the basis of the detection result of (b) above.

Because phenanthrenequinone and/or a derivative thereof is used, it is anticipated that the measurement result will be less susceptible to the effect of measurement interfering substances that are readily oxidizable in the liquid sample.

The following concentration measurement methods are further provided.

The concentration measurement method of the ninth invention is a method for measuring the concentration of a target substance contained in a liquid sample, comprising the steps of:

(a) bringing into contact the liquid sample, a dehydrogenase or an oxidase, and phenanthrenequinone and/or a derivative thereof;

(b) dehydrogenating or oxidizing the target substance contained in the liquid sample with the dehydrogenase or oxidase;

(c) accepting electrons from the dehydrogenase or oxidase with the phenanthrenequinone and/or derivative thereof;

(d) shining light on the phenanthrenequinone and/or derivative thereof that has accepted electrons in (c) above;

(e) measuring the amount of light emitted from the phenanthrenequinone and/or derivative thereof that has accepted electrons; and (f) calculating the concentration of the target substance on the basis of the amount of light emitted.

The concentration measurement method of the tenth invention is a method for measuring the concentration of a target substance contained in a liquid sample, comprising the steps of:

(a) bringing into contact the liquid sample, a dehydrogenase or oxidase, and phenanthrenequinone and/or a derivative thereof that is a first mediator;

(b) dehydrogenating or oxidizing the target substance contained in the liquid sample with the dehydrogenase or oxidase;

(c) accepting electrons from the dehydrogenase or oxidase with the phenanthrenequinone and/or derivative thereof;

(d) accepting electrons with a second mediator from the phenanthrenequinone and/or derivative thereof that has accepted electrons in (c) above;

(e) shining light on the second mediator that has accepted electrons in (d) above;

(f) measuring the amount of light emitted from the second mediator that has accepted electrons in (d) above; and (g) calculating the concentration of the target substance on the basis of the amount of light emitted.

The concentration measurement method of the eleventh invention is a method for measuring the concentration of a target substance contained in a liquid sample in which water is a solvent, comprising the steps of:

(a) dissolving in the liquid sample a quinone compound and an oxidase whose substrate is the target substance and which donates electrons to the quinone compound;

(b) detecting the current produced in the solution obtained in (a) above; and (c) calculating the concentration of the target substance on the basis of the detection result of (b) above.

The following sensors are further provided.

The sensor of the twelfth invention is a sensor for detecting or quantifying a target substance contained in a liquid sample, comprising a PQQ-dependent or FAD-dependent dehydrogenase, a quinone compound having a hydrophilic functional group, and at least first and second electrodes. The quinone compound comes into contact with at least part of the first electrode and with at least part of the second electrode. The PQQ-dependent or FAD-dependent dehydrogenase dehydrogenates (oxidizes) the target substance by coming into contact with the liquid sample. The quinone compound accepts electrons from the enzyme. When voltage is applied between the first and second electrodes, one of the electrodes accepts electrons from the quinone compound.

With the twelfth invention given above, since the sample, the enzyme, the quinone compound, and the first and second electrodes come into contact, when voltage is applied between the first and second electrodes, it is expected that one of the electrodes will become the working electrode, and the other will become the counter electrode.

The sensor of the thirteenth invention is a sensor for detecting or quantifying a target substance contained in a liquid sample, comprising in particular an enzyme, a quinone compound, and at least a pair of electrodes. The redox potential of the quinone compound measured using a silver/silver chloride (saturated potassium chloride) electrode as a reference electrode is negative below 0V.

The sensor of the fourteenth invention is a sensor for detecting or quantifying a target substance contained in a liquid sample, comprising in particular an enzyme, a quinone compound having a hydrophilic functional group, and at least a pair of electrodes. The redox potential of the quinone compound measured using a silver/silver chloride (saturated potassium chloride) electrode as a reference electrode is negative below 0V.

With the thirteenth and fourteenth inventions given above, since the redox potential of the quinone compound measured using a silver/silver chloride (saturated potassium chloride) electrode as a reference electrode is negative below 0V, the detection result is less apt to be affected by readily oxidizable measurement interfering substances in the liquid sample. Thus, it is anticipated that the target substance can be detected at a higher reliability.

The sensor of the fifteenth invention is a sensor for detecting or quantifying a target substance contained in a liquid sample, comprising a quinone compound having a hydrophilic functional group, an enzyme containing a coenzyme in the enzyme molecule, or to which a coenzyme is bonded, and at least a pair of electrodes. The enzyme dehydrogenates or oxidizes the target substance contained in the sample by coming into contact with the liquid sample. The quinone compound accepts electrons from the enzyme. When voltage is applied between the pair of electrodes, one of the electrodes accepts electrons from the quinone compound.

The present invention provides a sensor and a concentration measurement method with little measurement error, and allows target substance measurement to be performed very precisely.

DETAILED DESCRIPTION

Figure 1:
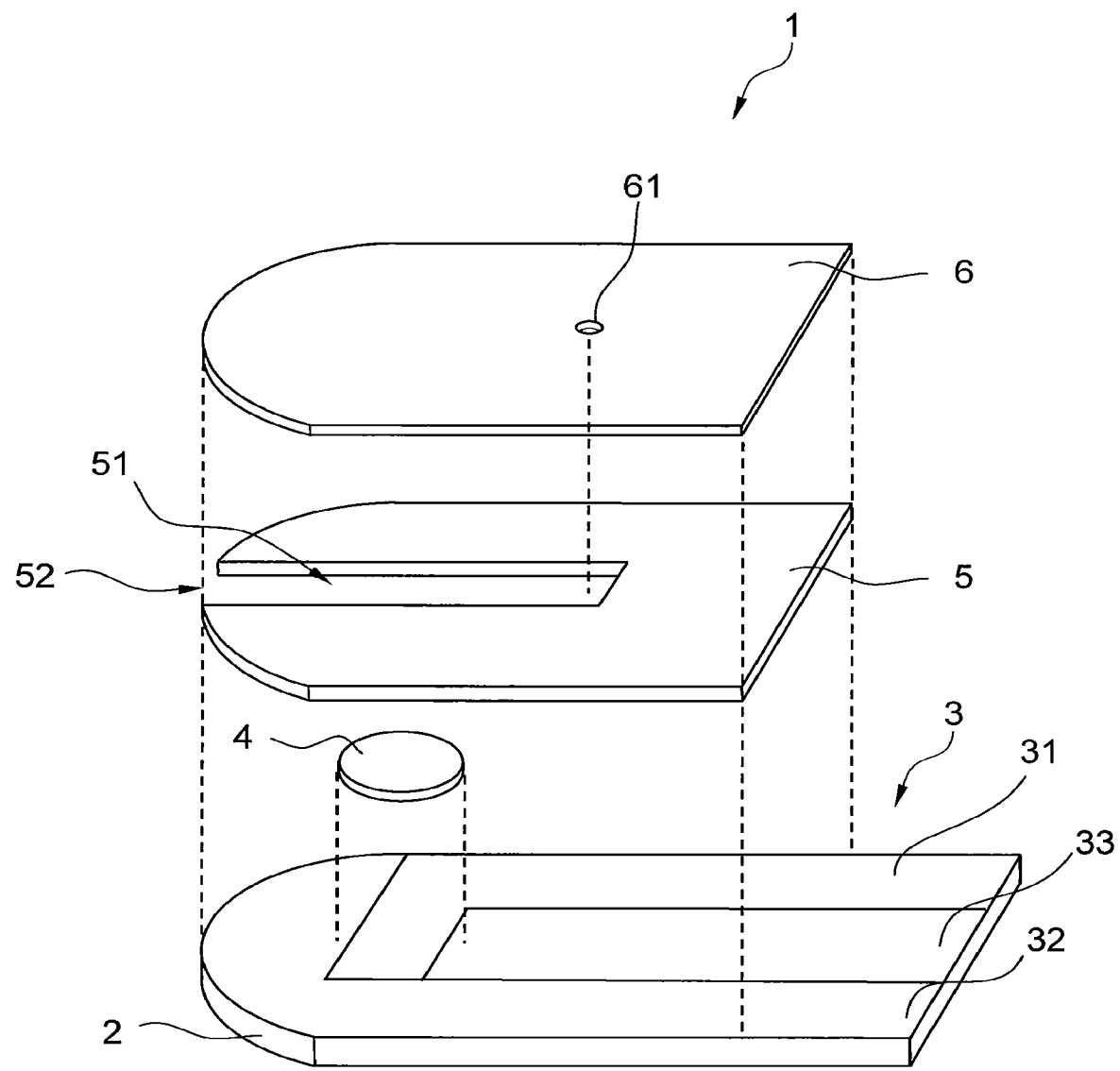
FIG. 1 is an exploded oblique view of the simplified configuration of a sensor.

[1] First Embodiment 1-1. Sensor 1-1-a. Simplified Configuration of Sensor

A sensor 1 is an example of a sensor comprising a quinone compound, an enzyme, and electrodes. The sensor 1 can detect and/or quantify a target substance in a liquid sample.

More specifically, the sensor 1 has a substrate 2, a conductive layer 3, a reagent layer 4, a spacer 5, and a cover 6.

1-1-b. Substrate

As shown in FIG. 1, the substrate 2 is a flat member. The substrate 2 has electrical insulation properties. Examples of the material that makes up the substrate 2 include polyethylene terephthalate, vinyl polymer, polyimide, polyester, styrenics, and other such resins; glass; and ceramics.

The substrate 2 is not limited to any specific dimensions. However, the width of the substrate 2 is preferably 4 to 20 mm, and more preferably 5 to 10 mm. The length of the substrate 2 is preferably 20 to 40 mm. The thickness of the substrate 2 is preferably 0.1 to 1 mm. The width, length, and thickness of the substrate 2 are all preferably within the above ranges.

1-1-c. Conductive Layer

As shown in FIG. 1, the conductive layer 3 is formed in a substantially uniform thickness over the substrate 2. The conductive layer 3 includes three electrodes 31 to 33. The electrode 31 is sometimes called a working electrode, the electrode 32 a counter electrode, and the electrode 33 a detecting electrode. The electrode 33 can be omitted.

A portion of each of the electrodes 31 to 33 is disposed so as to face a capillary 51.

The other portion of the electrodes 31 to 33 is exposed, that is, not covered by the spacer 5 and the cover 6, at the opposite end from an inlet 52 of the sensor 1. These exposed portions function as leads. That is, these exposed portions receive the application of voltage from a measurement device 101, and transmit current to the measurement device 101.

Each electrode may be formed by printing with a conductive material, or by covering the substrate 2 with a conductive material, and then forming a non-conductive track by laser ablation or the like. For example, the conductive layer 3 is formed by sputtering palladium onto the substrate 2, and a non-conductive track can be formed by laser ablation. The non-conductive track preferably has a width of 0.01 to 0.5 mm, and more preferably 0.05 to 0.3 mm.

There are no particular restrictions on the material that makes up the conductive layer 3, as long as it is a conductive material (conductive substance). Examples of conductive materials include metals, metal mixtures, alloys, metal oxides, metal compounds, and other such inorganic conductive substances; hydrocarbon-based conductive polymers, conductive polymers containing hetero atoms, and other such organic conductive substances; and combinations of these substances. The material that makes up the conductive layer 3 is preferably palladium, gold, platinum, carbon, or the like, with palladium being particularly favorable.

The thickness of the conductive layer 3 can be varied according to the constituent material and the formation method. For example, when the conductive layer 3 is formed by sputtering, the thickness of the conductive layer 3 is preferably 0.1 to 20 nm, and more preferably 1 to 10 nm. When the conductive layer 3 is formed by printing, the thickness of the conductive layer 3 is preferably 0.1 to 50 μm, and more preferably 1 to 30 μm.

1-1-d. Reagent Layer

As shown in FIG. 1, the reagent layer 4 is disposed so as to be in conduct with the electrodes 31 to 33. The reagent layer 4 functions as the active site of the sensor 1 along with the electrodes 31 and 32. The "active site" is the region that is electrochemically active, and is a portion that reacts with a specific substance in the liquid sample and produces an electrical signal. More specifically, the reagent layer 4 includes an enzyme and a mediator.

The reagent layer 4 may be disposed so as to come into contact with part of at least the electrodes 31 and 32 (the first electrode and second electrode). Also, the reagent layer 4 may be disposed so as to come into further contact with the electrode 33.

Enzyme

The reagent layer 4 contains one or more types of enzyme. The enzyme contained in the reagent layer 4 is preferably an enzyme whose substrate is the target substance, and more particularly, is preferably an enzyme that reacts specifically with the target substance. The enzyme donates electrons to the quinone compound according to the concentration of the target substance, that is, the amount of reaction with the target substance.

A redox enzyme is particularly favorable as the enzyme contained in the reagent layer 4. Specific examples of redox enzymes include oxidases and dehydrogenases whose substrate is the target substance. As to examples of these redox enzymes, if the target substance is glucose, then glucose oxidase or glucose dehydrogenase is preferable; if the target substance is lactic acid, then lactic acid oxidase or lactic acid dehydrogenase is preferable; if the target substance is cholesterol, then cholesterol esterase or cholesterol oxidase is preferable; if the target substance is an alcohol, then alcohol oxidase is preferable; and if the target substance is bilirubin, then bilirubin oxidase is preferable.

The reagent layer 4 may contain a coenzyme suited to the enzyme.

There are no particular restrictions on the enzyme as to its coenzyme dependence. For example, the enzyme contained in the reagent layer 4 may be an enzyme having dependence on NAD (nicotinamide adenine dinucleotide), NADP (nicotinamide adenine dinucleotide phosphate), PQQ (pyrroloquinoline quinone), FAD (flavin adenine dinucleotide), or another such coenzyme.

The coenzyme of the enzyme is preferably FAD or PQQ. With enzymes corresponding to these coenzymes, the coenzyme is either bonded to or contained in the enzyme protein thereof. Thus, there is no need to add the coenzyme separately from the enzyme during the production or measurement of the sensor. As a result, the sensor configuration, manufacturing process, and measurement process are all simplified.

With NAD- and NADP-dependent enzymes, as disclosed in Patent Literature 2, for example, coenzyme NAD and NADP that function in a state of not being bonded to an enzyme protein may be added separately. When a coenzyme is added separately, the sensor configuration and its manufacturing and measurement processes are more complicated than when using an enzyme whose coenzyme is FAD or PQQ. With the present invention, however, it is also possible to use NAD- and NADP-dependent enzymes.

For example, the enzyme may be an FAD-dependent oxidase; NAD-dependent, PQQ-dependent, or FAD-dependent dehydrogenase, or the like. Specific examples of oxidases and dehydrogenases are as given above.

The enzyme in the reagent layer 4 is not limited to these examples, and can be suitably selected according to the target substance.

The enzyme content in the reagent layer 4 is set so as to allow the detection of the target substance, and is preferably set to 0.2 to 20 U (units), and more preferably about 0.5 to 10 U, per measurement or per sensor.

Mediator

The reagent layer 4 contains one or more types of mediator. A mediator is also referred to as an electron acceptor or electron transmitting substance. A mediator can switch back and forth between an oxidant and a reductant. It is a substance that mediates the movement of electrons between substances, either directly or in conjunction with another mediator.

We will now describe the work of a mediator in a case in which the reagent layer 4 contains an enzyme that oxidizes a substrate. Upon oxidizing the substrate, the enzyme accepts electrons from the substrate, and donates electrons to the coenzyme. As a result, the coenzyme changes from an oxidant to a reductant. The mediator, which is an oxidant, accepts electrons from the coenzyme that has become a reductant, and returns the coenzyme to being an oxidant. As a result, the mediator itself becomes a reductant. The mediator that has become a reductant donates electrons to the electrode 31 or 32, and itself becomes an oxidant. Thus, the mediator mediates electron movement between the enzyme and the electrodes.

The coenzyme may be supported by an enzyme protein (enzyme molecule) by bonding to the enzyme protein. Also, the coenzyme may be present in a state of being separated from the enzyme protein.

A quinone compound is preferable as the mediator. A "quinone compound" is a compound that contains quinone. Quinone compounds include quinone and quinone derivatives. Examples of quinone derivatives include compounds in which various kinds of functional groups (also called substituents) have been added to quinone.

Examples of the quinone in the quinone compound include (a) benzoquinone, (b) naphthoquinone, (c) anthraquinone, (d) phenanthrenequinone, and (e) phenanthrolinequinone. A specific example of a phenanthrenequinone is 9,10-phenanthrenequinone. Specific examples of the structural formulas of various quinones are given below.

An example of an added functional group (substituent) in a quinone derivative is a hydrophilic functional group. Examples of hydrophilic functional groups include a sulfonic acid group (sulfo group, —$SO_3H$), a carboxylic acid group (carboxyl group, —COOH), and a phosphoric acid group (—$PO_4H_2$). Sulfonic acid groups, carboxylic acid groups, and phosphoric acid groups also include salts of these (sodium salts, potassium salts, calcium salts, etc.).

One quinone derivative may have two or more hydrophilic functional groups. Also, one quinone derivative may have two or more types of functional group.

The quinone derivative may have a substituent that includes a benzene ring. The above-mentioned hydrophilic functional group (including salts) may be added to a benzene ring in the substituent. In other words, the hydrophilic functional group may be bonded to the quinone via the benzene ring.

For example, one or more of the following substituents may be added to the above-mentioned quinones (a) to (e).

[First Chemical Formula]

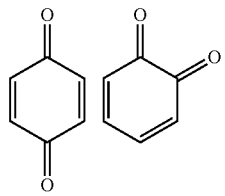
(a)

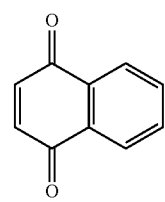
(b)

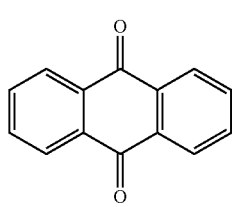
(c)

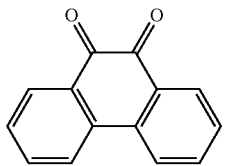
(d)

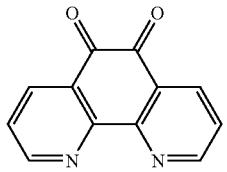
(e)

[Second Chemical Formula]

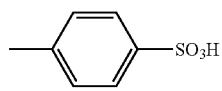
(G1)

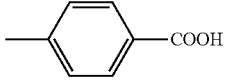
(G2)

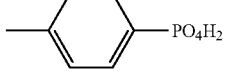
(G3)

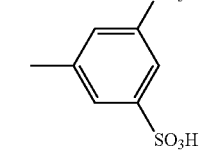
(G4)

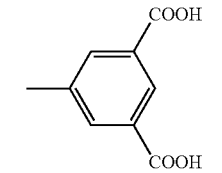
(G5)

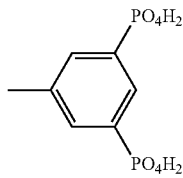

(G6)

In the substituent, two or more functional groups may be added to a single benzene ring, or two or more types of functional group may be added to a single benzene ring.

Figure 11:
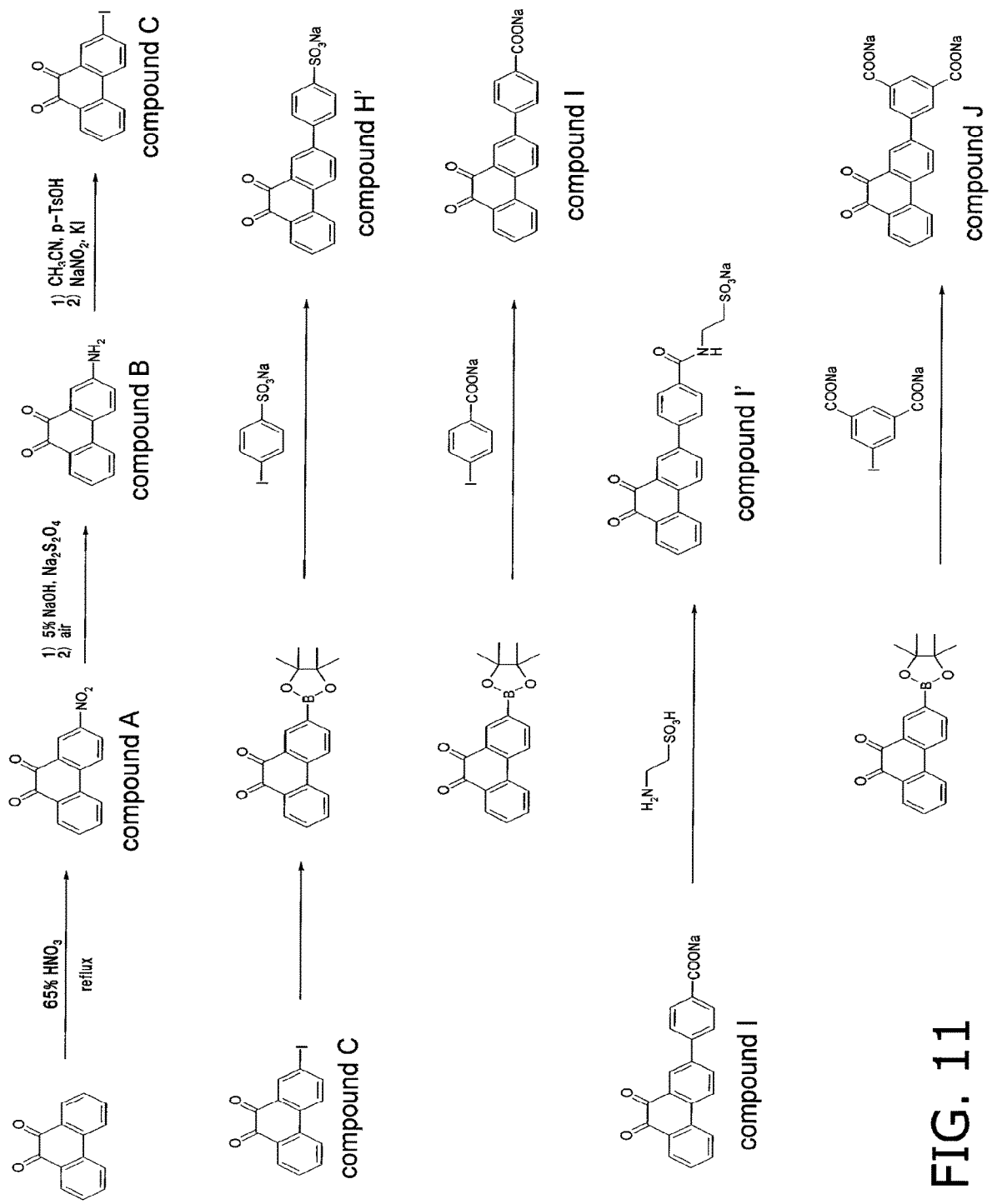
FIG. 11 is the synthesis path of a phenanthrenequinone derivative.

Furthermore, another atom may be interposed between the benzene ring and the above-mentioned hydrophilic functional group. For example, the compound I' shown in FIG. 11 is obtained by a condensation reaction between a compound I and aminoethanesulfonic acid. The substituents in compound I' have a sulfonic acid group, a benzene ring, and an aminocarboxyl (—CONH—) between the sulfonic acid group and the benzene ring.

There are no particular restrictions on the addition position in the quinone, be it a substituent having a benzene ring or a substituent that does not have a benzene ring. For example, with 9,10-phenanthrenequinone, it is preferable to select one position from among the 1, 2, 3, 4, and 7 positions.

The sensor 1 may have one or more compounds selected from the group consisting of 9,10-phenanthrenequinone-2-sulfonic acid, 9,10-phenanthrenequinone-1-sulfonic acid, 9,10-phenanthrenequinone-3-sulfonic acid, 9,10-phenanthrenequinone-4-sulfonic acid, 9,10-phenanthrenequinone-2,7-disulfonic acid, 9,10-phenanthrenequinone-2-carboxylic acid, and 9,10-phenanthrenequinone-2-phosphoric acid, as the quinone derivative.

The amount in which the quinone compound is contained in the reagent layer 4 can be set so as to allow function as a mediator, and is preferably set to 1 to 500 mmol, and more preferably about 10 to 200 mmol, per measurement or per sensor.

The amount of enzyme per measurement or per sensor is as discussed above. Thus, the amount of mediator per unit of enzyme is preferably 0.05 to 2500 nmol, and more preferably 1 to 400 nmol. It is particularly favorable for the amount of the quinone derivative (more specifically, the phenanthrolinequinone) to be within this range.

A conventional method can be favorably used as the method for manufacturing a quinone compound.

Quinone has been used in the past in the fields of medicine, agrochemicals, and industry. Quinone can be manufactured from an aromatic hydrocarbon, for example. More specifically, anthraquinone can be easily manufactured by the oxidation of anthracene.

Also, the method for manufacturing a quinone compound having a hydrophilic functional group may include a step of introducing the hydrophilic functional group into the quinone. For example, a method in which quinone is reacted with fuming sulfuric acid is an example of a method for adding a sulfonic acid group as a hydrophilic functional group to a quinone.

The sensor 1 may have two or more quinone compounds, and may have an electron transmitting substance other than a quinone compound.

In this embodiment, the quinone compound is contained in the reagent layer 4, but the quinone compound may instead be contained in the electrodes. A quinone compound having a hydrophilic functional group has higher water solubility than the quinone that is the main component of this quinone compound.

Also, the volatility of a quinone compound having a hydrophilic functional group tends to be lower than that of the quinone that is the main component of this quinone compound. Thus, if a hydrophilic functional group is added to a quinone compound, the quinone compound will be contained in the reagent layer 4, and can therefore function as a mediator.

Advantages of Quinone Compound Having a Hydrophilic Functional Group

A quinone compound having a hydrophilic functional group is suited to measurement of a target substance in a sample in which water is the solvent (such as blood).

If the mediator is a quinone compound having a hydrophilic functional group, the mediator molecules and the enzyme molecules have more opportunities to collide in the sample. As a result, the reaction velocity increases, there is an increase in the amount of current originating in the target substance, and measurement will take less time.

Also, if the mediator is a quinone compound having a hydrophilic functional group, a filler component or binder component, which is necessary for fixing the mediator, does not have to be provided in or on the working electrode. Specifically, if the mediator functions by dissolving into the sample, then the mediator can be easily disposed on the electrodes by dropping the mediator solution onto the electrodes and drying, as discussed above.

The mediator is preferably disposed so as to be in contact with at least part of the first electrode and at least part of the second electrode, out of the electrodes constituting the sensor. The first electrode and second electrode correspond to the working electrode and counter electrode. Thus disposing the mediator stabilizes the potential of the electrodes, so measurement accuracy is better. Since an electrochemical reaction proceeds and measurement is carried out by applying voltage between the first and second electrodes, if the mediator is touching part of the two electrodes, a stable mediator reduction potential will be imparted to the electrodes by a reduction reaction of the mediator at the electrode on the side that functions as the counter electrode. On the other hand, the potential of the electrode on the side that functions as the working electrode is the result of adding the above-mentioned applied voltage to the reduction potential of the mediator, and the potential will be more stable.

When the long-term stability of the sensor and so forth are taken into account, a quinone to which a hydrophilic functional group has not been added is preferably contained in the electrodes. Specifically, the electrodes are preferably formed from a mixture of quinone and a conductive material. There is a known method in which a filler component or binder component is added, and the mediator molecules are fixed in the working electrode or on the working electrode.

Favorable Range of Redox Potential of Mediator, and Advantages Thereof

An interfering substance is a substance that interferes with the accurate detection of a target substance by the sensor 1. Examples of interfering substances include ascorbic acid, uric acid, and acetaminophen. If the object of measurement is a non-biological sample (a sample other than blood, urine, or other such biological sample), then interfering substances are readily oxidizable substances contained in that non-biological sample.

As discussed above regarding prior art, if the potential required to oxidize an interfering substance is lower than the potential required to oxidize the mediator, the interfering substance will affect the measurement result of the sensor. This produces error in the measurement result. For instance if the sample is blood, an error will be caused if the electrode potential required to oxidize the mediator is significantly higher (more positive) than the electrode potential required to oxidize ascorbic acid or the like contained in the blood.

The electrode potential required to oxidize the mediator depends on the redox potential of the mediator itself. Thus, it is preferable, in terms of reducing the effect of interfering substances, for the redox potential of the mediator to be more negative. Even if it is more positive than the oxidation potential of the interfering substances, the effect of the interfering substances can be reduced by using a mediator having a redox potential as close as possible to that oxidation potential. To reduce this effect even more, it is preferable to use a mediator having a redox potential that is more negative than the oxidation potential of the interfering substances.

Also, if the enzyme oxidizes the target substance, the redox potential of the mediator is preferably more positive than that of the coenzyme. This allows the mediator to easily accept electrons from the coenzyme.

If the enzyme reduces the target substance, the redox potential of the mediator is preferably more negative than that of the coenzyme. This allows the mediator to easily donate electrons to the coenzyme. When the target substance is thus detected by a reduction reaction, the relation between the potentials of the coenzyme, the mediator, and the interfering substances (readily oxidizable substances) will be the opposite from that when the target substance is detected by oxidation. A case in which the target substance is detected by oxidation will now be described.

The specific redox potential of the coenzyme is as follows. FAD and PQQ, which are coenzymes, typically function in conjunction with an enzyme protein in a state of being bonded to the enzyme protein. The redox potential of these coenzymes is approximately −300 and approximately −200 mV, respectively. NAD functions without bonding to an enzyme protein. The redox potential of NAD is approximately −520 mV.

Furthermore, the ability of a mediator to accept electrons tends to be better the more positive the redox potential of the mediator is with respect to the coenzyme. Specifically, the greater is the difference between the redox potential of the mediator and that of the coenzyme, the greater is the difference in the energy levels. Thus, the mediator accepts electrons faster. Therefore, in terms of increasing the measurement sensitivity and speed of a sensor, it is preferable for the redox potential of the mediator to be high on the positive side.

In order to realize a sensor and measurement method with good sensitivity and little error, as discussed above, the positive side of the redox potential of the mediator is limited by the redox potential of the interfering substances, and the negative side by the redox potential of the coenzyme, which is related to the ability to accept electrons. This range is sometimes extremely narrow.

For example, in Patent Literature 2 is disclosed a sensor having phenanthroline quinone as a mediator, which is a heterocyclic compound containing nitrogen atoms, and having an NAD-dependent enzyme. The redox potential of phenanthroline quinone is approximately 0 mV, and that of NAD is approximately −520 mV, that is, there is a potential difference of approximately 520 mV between the mediator and the coenzyme. Since the oxidation potential of ascorbic acid is approximately −140 mV, if the mediator is phenanthroline quinone, the effect of interfering substances cannot be completely avoided, for the reasons given above.

As discussed above, a sensor having a PQQ-dependent or FAD-dependent enzyme has an advantage in that it can be manufactured at low cost. However, since PQQ and FAD have a higher redox potential than NAD, it is not easy to find a mediator with a low potential that can be applied to PQQ-dependent and FAD-dependent enzymes. At present there is a need for a mediator with a low redox potential that can be applied to PQQ-dependent and FAD-dependent enzymes as well, in order to reduce the effect of interfering substances and to keep manufacturing costs low.

However, if the coenzyme is FAD or PQQ, since the potential of these is more on the positive side, the above-mentioned range is particularly narrow.

The redox potentials of the 9,10-phenanthrenequinone, 9,10-phenanthrenequinone-2-sulfonic acid, 1,2-naphthoquinone-4-sulfonic acid, and 2,5-dimethyl-1,4-benzoquinone that are examples of the mediator pertaining to the present invention are −180 mV, −140 mV, −16 mV, and −5 mV, respectively. These redox potentials are more negative than 0 mV, more positive than the potential of NAD, and more positive than the potential of FAD and PQQ. In particular, the redox potentials of 9,10-phenanthrenequinone and 9,10-phenanthrenequinone-2-sulfonic acid are more negative than the oxidation potential of ascorbic acid (approximately −140 mV). Specifically, these mediators can be applied to a sensor having a PQQ-dependent or FAD-dependent enzyme. Also, these mediators can reduce the effect that interfering substances have on the detection result.

However, the ability to accept electrons from the coenzyme is not determined by the potential relation alone. The ability of a quinone compound to accept electrons is also affected by the relation between the electrical charge of the quinone compound and the charge near the active site of the enzyme, the relation between the size of the quinone compound molecules and the size of the active site space of the enzyme, for example.

If the enzyme is an FAD-dependent enzyme or a PQQ-dependent enzyme, the mediator is preferably 9,10-phenanthrenequinone (including its derivatives). Phenanthrenequinone has a compact molecular size, and the aromatic rings are not linked in a single lateral row as with anthraquinone. Thus, it is surmised that 9,10-phenanthrenequinone can readily work its way into the active site space of the enzyme. Also, since 9,10-phenanthrenequinone does not have an electrical charge, it is predicted that it will not be susceptible to the effect of a charge at the active site of the enzyme.

Other Compositions

The reagent layer 4 may contain other components besides an enzyme and a mediator. These components can be any of a variety of substances that can improve the storage stability of the enzyme or mediator or raise the reactivity between the enzyme and the target substance. A buffer is an example of such a component.

Method for Forming Reagent Layer

The reagent layer 4 can be formed by various methods. Examples include printing and coating.

An example of a formation method will now be discussed. An aqueous solution containing an enzyme, a mediator, and any other components that are necessary is dropped in a specific amount onto the electrodes 31 and 32 using a microsyringe or the like, after which it is allowed to stand in a suitable environment to dry, thereby forming the reagent layer 4. The aqueous solution may also be dropped onto the electrode 33 if needed.

The amount in which the aqueous solution is dropped is not limited to any specific numerical value, but is preferably 0.5 to 5 µl, and more preferably 1 to 2 µL.

The reagent layer 4 is not limited to any specific shape. This shape may be rectangular, circular, etc. The surface area of the reagent layer 4 (the surface area in the planar direction of the substrate 2) is determined according to the size and characteristics of the device. This area is preferably 1 to 25 mm$^2$, and more preferably 2 to 10 mm$^2$.

The amounts in which the enzyme, mediator, and other components are contained in the aqueous solution coating are selected according to the required size and characteristics of the device.

1-1-e. Spacer

As shown in FIG. 1, the spacer 5 is used to provide a gap between the cover 6 and the conductive layer 3.

More specifically, the spacer 5 is a flat member that covers the entire conductive layer 3 except for the capillary 51 portion (discussed below) and the lead portion of the electrodes 31 to 33. The spacer 5 has a rectangular cut-out that exposes the opposite end from that of the lead portion of the electrodes 31 to 33. Because the spacer 5 has this cut-out, it forms the capillary 51, which is surrounded by the spacer 5, the conductive layer 3, and the cover 6. Thus, the spacer 5 provides the side walls of the capillary 51, and also defines the length, width, height, etc., of the capillary 51.

The volume of the capillary 51 is preferably set to about 0.1 to 1.0 µL (microliter). The thickness of the spacer 5 is preferably 0.1 to 0.2 mm, the length of the cut-out in the spacer is preferably 1 to 5 mm, and the width of the spacer is preferably 0.5 to 2 mm. These dimensions may be suitably selected so that the capillary 51 will have the desired volume. For instance, if the spacer 5 has a thickness of 0.145 mm and has a cut-out with a length of 3.4 mm and a width of 1.2 mm, then the resulting capillary 51 will have a length of 3.4 mm, a width of 1.2 mm, a height of 0.145 mm, and a volume of 0.6 pt.

The capillary 51 draws in the liquid sample by capillary action through the inlet 52 (the opening of the capillary 51), and supports this sample on the electrodes 31 to 33.

1-1-f. Cover

As shown in FIG. 1, the cover 6 is a flat member that covers the entire spacer 5. The cover 6 has a hole that goes from the front to the back. This hole functions as a vent hole 61 that leads from the capillary 51 to the outside. The vent hole 61 is an exhaust hole for discharging air inside the capillary 51 to outside the capillary when a liquid sample is drawn into the capillary 51. Thus discharging the air makes it easier for the liquid sample to be drawn into the capillary 51. The vent hole 61 is preferably provided at a position that is away from the inlet 52, that is, at the back of the capillary 51 as seen from the inlet 52. Thus disposing the inlet 52 allows the liquid sample to move quickly from the inlet 52 to the back of the capillary 51.

1-2. Measurement System

Figure 2:
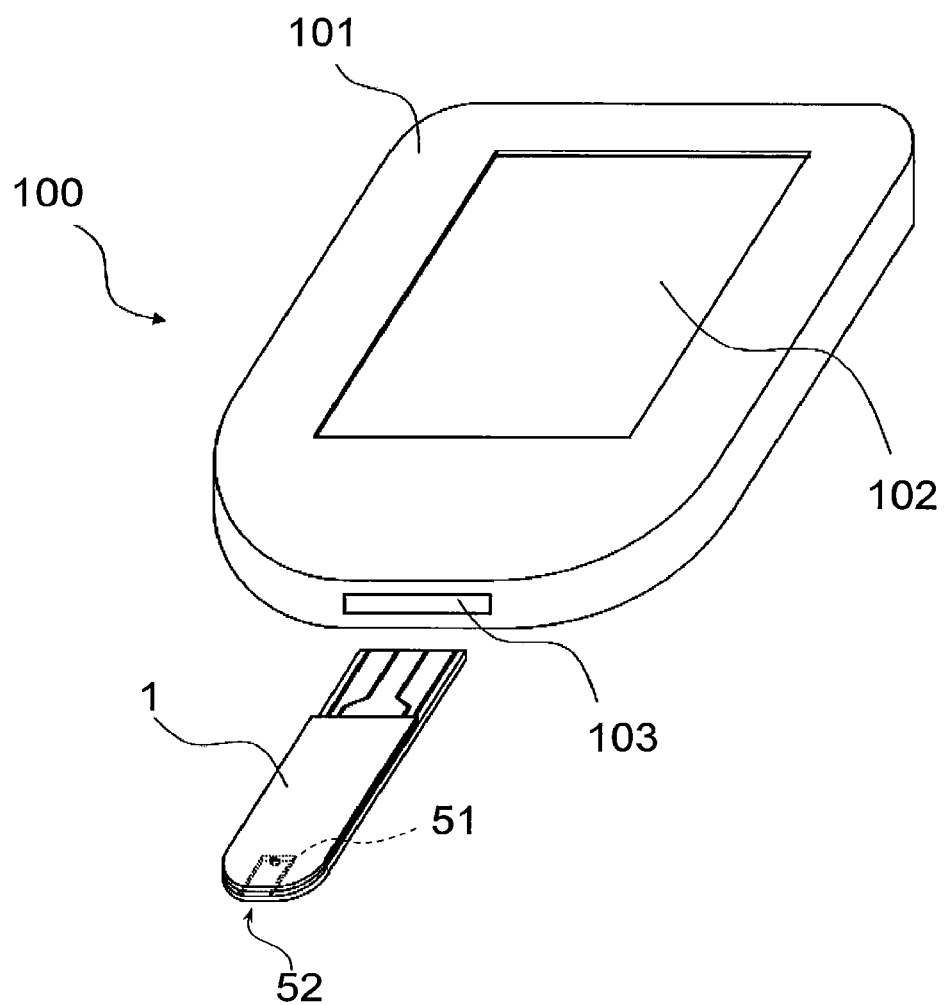
FIG. 2 is an oblique view of the simplified configuration of a measurement system.

The above-mentioned sensor 1 is used in the measurement system 100 shown in FIG. 2. The measurement system 100 has the sensor 1 and the measurement device 101.

Figure 3:
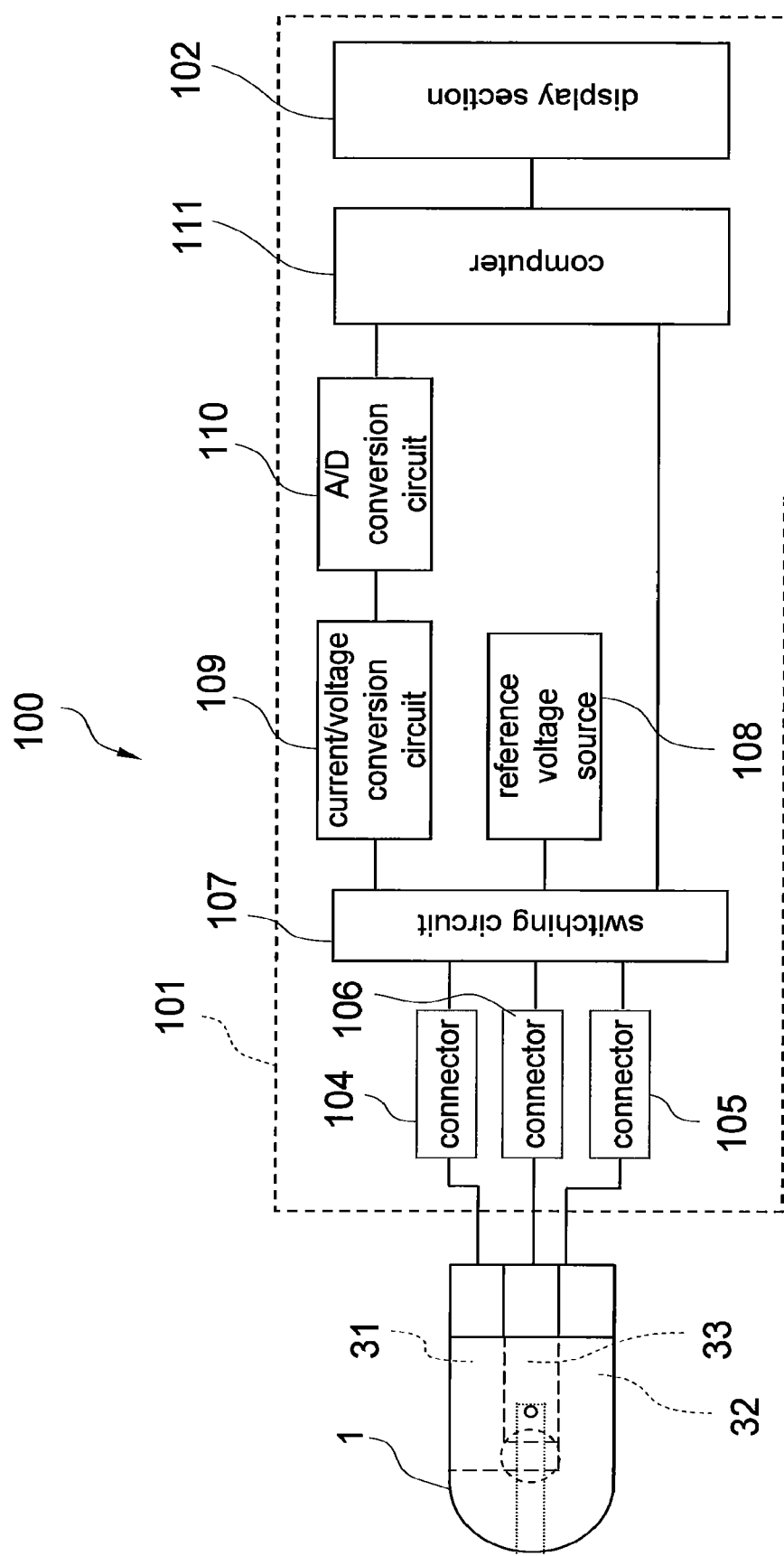
FIG. 3 is a diagram illustrating of the simplified configuration of a measurement system.

As shown in FIGS. 2 and 3, the measurement device 101 comprises a display unit 102, a mounting unit 103, a switching circuit 107, a reference voltage source 108, a current/voltage conversion circuit 109, an A/D conversion circuit 110, and a computer 111. The measurement device 101 has connectors corresponding to the electrodes of the sensor 1. Connectors 104 to 106 are depicted in FIG. 3.

The display unit 102 displays the status of the measurement device 101, measurement results, operational content, and so forth. More specifically, the display unit 102 is constituted by a liquid crystal display panel.

As shown in FIG. 2, the sensor 1 is removably inserted into the mounting section 103.

As shown in FIG. 3, the connectors 104 to 106 are connected to the electrodes 31 to 33 of the sensor 1, respectively by mounting the sensor 1 in the mounting section 103.

A switching circuit 107 connects the connectors 104 to 106 to a reference voltage source 108, or is connected to a current/voltage conversion circuit 109.

The reference voltage source 108 applies voltage to the electrodes 31 to 33 via the connectors 104 to 106.

The current/voltage conversion circuit 109 receives current from the sensor 1 via the connectors 104 to 106, converts this into voltage, and outputs this to an A/D conversion circuit 110.

The A/D conversion circuit 110 converts the output value (analog value) from the current/voltage conversion circuit 109 into a pulse (digital value).

The computer 111 has a CPU (central processing unit, as well as a ROM (read only memory), RAM (random access memory), and other such recording media. The computer 111 calculates the concentration of the target substance, and controls the operation of the various components in the measurement device 101.

The concentration calculation function of the computer 111 will be described. The storage medium of the computer 111 stores a conversion table used for deciding the concentration of the target substance in the sample, a correction amount table used for deciding the correction amount of this concentration, and so forth. The computer 111 refers to this conversion table and calculates the temporary concentration of the target substance on the basis of a pulse from the A/D conversion circuit 110. The computer 111 uses the correction amount in the correction amount table to decide the final concentration of the target substance. The concentration thus calculated is displayed on the display section 102.

Also, the computer 111 has functions besides its concentration calculation function, such as controlling the switching of the switching circuit 107, controlling the voltage of the reference voltage source 108, keeping time during concentration measurement and correction amount selection (timer function), outputting display data to the display section 102, and communicating with external devices.

The various functions of the computer 111 are realized by having the CPU read and execute programs stored in the ROM, etc. (not shown).

1-3. Use of Measurement System

The measurement of concentration with the measurement system 100 will now be described.

When the sensor 1 is plugged into the mounting section 103, the connectors 104 to 106 are connected to the electrodes 31 to 33, respectively. Also, a switch (not shown) inside the mounting section 103 is depressed by the sensor 1. When this switch is pressed, the computer 111 determines that the sensor 1 has been mounted, and puts the measurement device 101 in a sample standby state. This sample standby state refers to a state in which voltage application between the working electrode 31 and the detecting electrode 33 has been begun by the reference voltage source 108 under the control of the computer 111 and via the connectors 104 and 106, and the current/voltage conversion circuit 109 has begun the measurement of current, but the liquid sample has yet to be supplied for measurement.

When the user deposits a liquid sample in the inlet 52 of the sensor 1, the liquid sample is drawn in through the inlet 52 to the capillary 51 by capillary action.

Blood, perspiration, urine, and other biological liquid samples, environmental liquid samples, and food liquid samples, for example, can be used as the liquid sample. For instance, if the sensor 1 is used as a blood glucose level sensor, the user pricks his finger, palm, arm, or the like and squeezes out a small amount of blood, and this blood is used as a liquid sample for measurement in the sensor 1.

When the liquid sample reaches the working electrode 31 and the detecting electrode 33, there is a change in the current value received by the computer 111 via the current/voltage conversion circuit 109. The computer 111 determines from this change that a liquid sample has been drawn into the sensor 1. Measurement begins when it is thus detected that a liquid sample has been drawn in.

Inside the sensor 1, the enzyme, mediator, and other components in the reagent layer 4 dissolve in the liquid sample. This brings the liquid sample, the enzyme, and the mediator into contact with each other on the electrodes 31 and 32 of the sensor 1.

Control by the computer 111 causes the switching circuit 107 to connect the connectors 104 and 105 to the reference voltage source 108 and the current/voltage conversion circuit 109. This results in voltage being applied between the working electrode 31 and the counter electrode 32, and the current produced between the working electrode 31 and the counter electrode 32 is transmitted to the current/voltage conversion circuit 109.

The current that flows to the current/voltage conversion circuit 109 is converted into voltage. This voltage is further converted into a pulse by the A/D conversion circuit 110. The computer 111 calculates the concentration of a specific component from this pulse. The value calculated by the computer 111 is displayed on a display section 202. Other information may also be displayed for the user at the same time.

Upon completion of the measurement, the user can remove the sensor 1 from the mounting section 103.

The reference voltage source 108 is designed to provided enough voltage to induce the targeted electrochemical reaction between the two electrodes 31 and 32. This voltage is mainly set according to the chemical reaction and electrodes being used.

As is clear from the above description, when the measurement system 100 is used, a concentration measurement method is executed that includes:

(a) bringing a liquid sample, a mediator, and an enzyme into contact, (b) detecting the current produced by (a) above, and (c) measuring the concentration of a target substance on the basis of the detection result in (b) above.

Also, if the liquid sample is one in which water is the solvent, the measurement system 100 executes a concentration measurement method that includes:

(i) dissolving in the liquid sample a quinone compound and an oxidase whose substrate is the target substance and which donates electrons to the quinone compound, (ii) detecting the current produced in the solution obtained in (i) above; and (iii) calculating the concentration of the target substance on the basis of the detection result in (ii) above.

1-4. Conclusion

As is clear from the above description, the sensor 1 is a sensor for detecting or quantifying a target substance contained in a liquid sample, comprising a quinone compound, an enzyme that donates electrons to the quinone compound, and electrodes that accept electrons from the quinone compound. The target substance can become the substrate of the enzyme. The constitution of the sensor 1 may be expressed as comprising an enzyme whose substrate is a target substance, electrodes, and a quinone compound that transmits electrons between the enzyme and the electrodes.

This embodiment can further be expressed as follows.

(1)

A sensor for detecting or quantifying a target substance contained in a liquid sample, comprising:

a PQQ-dependent or FAD-dependent enzyme;

a quinone compound having a hydrophilic functional group; and at least a pair of electrodes, wherein the PQQ-dependent or FAD-dependent enzyme dehydrogenates or oxidizes the target substance by coming into contact with the liquid sample, the quinone compound accepts electrons from the PQQ-dependent or FAD-dependent enzyme, and when voltage is applied between the pair of electrodes, one of the electrodes accepts electrons from the quinone compound.

If two or more pairs of electrodes are provided, voltage may be applied to at least one of these pairs of electrodes.

(2)

The sensor according to (1) above, wherein the PQQ-dependent or FAD-dependent enzyme is a dehydrogenase.

(3)

The sensor according to (1), wherein the FAD-dependent enzyme is glucose dehydrogenase.

(4)

A sensor for detecting or quantifying a target substance contained in a liquid sample, comprising:

a quinone compound having a hydrophilic functional group;

an oxidase; and at least a pair of electrodes, wherein the oxidase oxidizes the target substance by coming into contact with the liquid sample, the quinone compound accepts electrons from the oxidase, and when voltage is applied between the pair of electrodes, one of the electrodes accepts electrons from the quinone compound.

(5)

The sensor according to (4) above, wherein the oxidase is an FAD-dependent enzyme.

(6)

A sensor for detecting or quantifying a target substance contained in a liquid sample, comprising:

a quinone compound having a hydrophilic functional group;

a dehydrogenase; and at least a pair of electrodes, wherein the dehydrogenase dehydrogenates the target substance by coming into contact with the liquid sample, the quinone compound accepts electrons from the dehydrogenase, and when voltage is applied between the pair of electrodes, one of the electrodes accepts electrons from the quinone compound.

(7)

The sensor according to any of (1) to (6) above, wherein the quinone compound has quinone and a substituent, and the substituent has a benzene ring and the hydrophilic functional group added to the benzene ring.

(8)

The sensor according to any of (1) to (7), wherein the quinone compound has at least one type of functional group selected from the group consisting of a sulfonic acid group, a carboxylic acid group, and a phosphoric acid group as the hydrophilic functional group.

(9)

The sensor according to (8) above, wherein the sulfonic acid group is at least one type of functional group selected from the group consisting of 2-sulfonic acid, 1-sulfonic acid, 3-sulfonic acid, 4-sulfonic acid, and 2,7-disulfonic acid, the carboxylic acid group is 2-carboxylic acid, and the phosphoric acid group is 2-phosphoric acid.

(10)

A sensor for detecting or quantifying a target substance contained in a liquid sample, comprising:

phenanthrenequinone and/or a derivative thereof as a mediator;

an enzyme; and at least a pair of electrodes, wherein the enzyme dehydrogenates or oxidizes the target substance by coming into contact with the liquid sample, the phenanthrenequinone and/or derivative thereof accepts electrons from the enzyme, and when voltage is applied between the pair of electrodes, one of the electrodes accepts electrons from the phenanthrenequinone and/or derivative thereof.

(11)

The sensor according to (10) above, wherein the phenanthrenequinone is 9,10-phenanthrenequinone, and the phenanthrenequinone derivative is a 9,10-phenanthrenequinone derivative.

(12)

The sensor according to (10) or (11) above, wherein the phenanthrenequinone derivative has a hydrophilic functional group.

(13)

The sensor according to (12) above, wherein the phenanthrenequinone derivative has at least one type of functional group selected from the group consisting of a sulfonic acid group, a carboxylic acid group, and a phosphoric acid group as the hydrophilic functional group.

(14)

The sensor according to any of (10) to (13) above, comprising, as the phenanthrenequinone derivative, at least one type of compound selected from the group consisting of:

9,10-phenanthrenequinone-2-sulfonic acid,
9,10-phenanthrenequinone-1-sulfonic acid,
9,10-phenanthrenequinone-3-sulfonic acid,
9,10-phenanthrenequinone-4-sulfonic acid,
9,10-phenanthrenequinone-2,7-disulfonic acid,
9,10-phenanthrenequinone-2-carboxylic acid, and
9,10-phenanthrenequinone-2-phosphoric acid.

(15)

The sensor according to any of (10) to (14) above, wherein the enzyme is a redox enzyme.

(16)

The sensor according to (15) above, wherein the redox enzyme is an oxidase.

(17)

The sensor according to (16) above, wherein the redox enzyme is an FAD-dependent oxidase.

(18)

The sensor according to (15) above, wherein the redox enzyme is a dehydrogenase.

(19)

The sensor according to (18) above, comprising at least one type of enzyme selected from the group consisting of an NAD-dependent dehydrogenase, a PQQ-dependent dehydrogenase, and an FAD-dependent dehydrogenase as the redox enzyme.

(20)

The sensor according to (19) above, wherein the redox enzyme is an FAD-dependent glucose dehydrogenase.

(21)

The sensor according to (15) above, wherein the redox enzyme is a PQQ-dependent or FAD-dependent enzyme.

(22)

The sensor according to any of (10) to (21) above, wherein the amount in which the phenanthrenequinone and a derivative thereof are contained in the sensor is 0.05 to 2500 nmol per unit of the enzyme.

(23)

The sensor according to any of (9) to (21) above, wherein the amount in which the phenanthrenequinone and a derivative thereof are contained in the sensor is 1 to 400 nmol per unit of the enzyme.

(24)

A method for measuring the concentration of a target substance contained in a liquid sample, comprising the steps of:

(a) bringing into contact the liquid sample, a PQQ-dependent or FAD-dependent enzyme, and a quinone compound having a hydrophilic functional group;

(b) dehydrogenating or oxidizing the target substance contained in the liquid sample with the PQQ-dependent or FAD-dependent enzyme;

(c) accepting electrons from the PQQ-dependent or FAD-dependent enzyme with the quinone compound;

(d) applying voltage to a pair of electrodes in contact with the liquid sample;

(e) oxidizing the quinone compound that has accepted electrons in (c) above with one of the pair of electrodes;

(f) measuring the current flowing between the pair of electrodes; and (g) calculating the concentration of the target substance on the basis of the current.

(25)

A method for measuring the concentration of a target substance contained in a liquid sample, comprising the steps of:

(a) bringing into contact the liquid sample, a quinone compound having a hydrophilic functional group, and an oxidase whose substrate is the target substance and which donates electrons to the quinone compound;

(b) detecting the current produced by (a) above; and (c) calculating the concentration of the target substance on the basis of the detection result of (b) above.

(26)

A method for measuring the concentration of a target substance contained in a liquid sample, comprising the steps of:

(a) bringing into contact the liquid sample, a quinone compound having a hydrophilic functional group, and a dehydrogenase whose substrate is the target substance and which donates electrons to the quinone compound;

(b) detecting the current produced by (a) above; and (c) calculating the concentration of the target substance on the basis of the detection result of (b) above.

(27)

A method for measuring the concentration of a target substance contained in a liquid sample, comprising the steps of:

(a) bringing into contact the liquid sample, phenanthrenequinone and/or a derivative thereof, and an enzyme whose substrate is the target substance and which donates electrons to the phenanthrenequinone and/or derivative thereof;

(b) detecting the current produced by (a) above; and (c) calculating the concentration of the target substance on the basis of the detection result of (b) above.

(28)

A sensor for detecting or quantifying a target substance contained in a liquid sample, comprising:

a PQQ-dependent or FAD-dependent dehydrogenase;

a quinone compound having a hydrophilic functional group; and at least first and second electrodes, wherein the quinone compound comes into contact with at least part of the first electrode and with at least part of the second electrode, the PQQ-dependent or FAD-dependent dehydrogenase dehydrogenates the target substance by coming into contact with the liquid sample, the quinone compound accepts electrons from the PQQ-dependent or FAD-dependent enzyme, and when voltage is applied between the first and second electrodes, one of the electrodes accepts electrons from the quinone compound.

(29)

A sensor for detecting or quantifying a target substance contained in a liquid sample, comprising:

an enzyme;

a quinone compound; and at least a pair of electrodes, wherein the redox potential of the quinone compound measured using a silver/silver chloride (saturated potassium chloride) electrode as a reference electrode is negative below 0V, the enzyme dehydrogenates or oxidizes the target substance by coming into contact with the liquid sample, the quinone compound accepts electrons from the enzyme, and when voltage is applied between the pair of electrodes, one of the electrodes accepts electrons from the quinone compound.

(30)

A sensor for detecting or quantifying a target substance contained in a liquid sample, comprising:

an enzyme;

a quinone compound having a hydrophilic functional group; and at least a pair of electrodes, wherein the redox potential of the quinone compound measured using a silver/silver chloride (saturated potassium chloride) electrode as a reference electrode is negative below 0V, the enzyme dehydrogenates or oxidizes the target substance contained in the liquid sample by coming into contact with the liquid sample, the quinone compound accepts electrons from the enzyme, and when voltage is applied between the pair of electrodes, one of the electrodes accepts electrons from the quinone compound.

(31)

A sensor for detecting or quantifying a target substance contained in a liquid sample, comprising:

a quinone compound having a hydrophilic functional group;

an enzyme containing a coenzyme in the enzyme molecule, or to which a coenzyme is bonded; and at least a pair of electrodes, wherein the enzyme dehydrogenates or oxidizes the target substance by coming into contact with the liquid sample, the quinone compound accepts electrons from the enzyme, and when voltage is applied between the pair of electrodes, one of the electrodes accepts electrons from the quinone compound.

(32)

The sensor according to (30) above, wherein the enzyme is a dehydrogenase.

(33)

A method for measuring the concentration of a target substance contained in a liquid sample in which water is a solvent, comprising the steps of:

(a) dissolving in the liquid sample a quinone compound and an oxidase whose substrate is the target substance and which donates electrons to the quinone compound;

(b) detecting the current produced in the solution obtained in (a) above; and (c) calculating the concentration of the target substance on the basis of the detection result in (b) above.

[2] Second Embodiment

The method pertaining to this embodiment is a method for measuring the concentration of a target substance contained in a liquid sample, comprising the steps of:

(a) bringing into contact the liquid sample, a dehydrogenase or an oxidase, and phenanthrenequinone and/or a derivative thereof;

(b) dehydrogenating or oxidizing the target substance contained in the liquid sample with the dehydrogenase or oxidase;

(c) accepting electrons from the dehydrogenase or oxidase with the phenanthrenequinone and/or derivative thereof;

(d) shining light on the phenanthrenequinone and/or derivative thereof that has accepted electrons in (c) above;

(e) measuring the amount of light emitted from the phenanthrenequinone and/or derivative thereof that has accepted electrons; and (f) calculating the concentration of the target substance on the basis of the amount of light.

If the liquid sample being used is one in which water is the solvent, the above-mentioned (a) may include: dissolving in the liquid sample phenanthrenequinone and/or a derivative thereof and an oxidase whose substrate is the target substance and which donates electrons to the phenanthrenequinone and/or a derivative thereof.

The "derivative of phenanthrenequinone" has already been described in the first embodiment.

The PQQ-dependent dehydrogenase and FAD-dependent dehydrogenase have also already been described in the first embodiment.

The measurement of the amount of light in (e) above is accomplished as follows. The liquid sample is added to a translucent cell containing an enzyme and phenanthrenequinone and/or a derivative thereof. This cell can be a commercially available optical measurement cell made of glass or polystyrene, for example. Light is shined on the cell using a commercially available spectrophotometer to detect the light that passes through. The wavelengths of the emitted light and the detected light are preferably selected to be a wavelength that exhibits a major change in absorbance along with the oxidation and reduction of the phenanthrenequinone and/or a derivative thereof. Consequently, the increase in reductant or decrease in oxidant of the phenanthrenequinone or derivative thereof, which accompanies the oxidation of the target substance, can be detected from the light. Here, an example of using phenanthrenequinone and/or a derivative thereof was discussed, but any quinone compound that accepts electrons from an enzyme and whose optical characteristics change as a result of reduction can be used.

Also, (f) above is accomplished by a computer that uses a calibration curve obtained with a reference solution having a known target substance concentration to calculate the concentration of the target substance.

[3] Third Embodiment

The concentration measurement method pertaining to this embodiment has the same constitution as the method in the second embodiment, except that a first mediator and a second mediator are used.

Specifically, the concentration measurement method of this embodiment is a method for measuring the concentration of a target substance contained in a liquid sample, comprising the steps of:

(a) bringing into contact the liquid sample, a dehydrogenase or oxidase, and phenanthrenequinone and/or a derivative thereof that is a first mediator;

(b) dehydrogenating or oxidizing the target substance with the dehydrogenase or oxidase;

(c) accepting electrons from the dehydrogenase or oxidase with the phenanthrenequinone and/or derivative thereof;

(d) accepting electrons with a second mediator from the phenanthrenequinone and/or derivative thereof that has accepted electrons in (c) above;

(e) shining light on the second mediator that has accepted electrons in (d) above;

(f) measuring the amount of light emitted from the second mediator that has accepted electrons in (d) above; and (g) calculating the concentration of the target substance on the basis of the amount of light.

Just as in the second embodiment, if the method of this embodiment is used with a liquid sample in which water is the solvent, step (a) above may include: dissolving in the liquid sample a quinone compound and an oxidase whose substrate is the target substance and which donates electrons to the quinone compound.

Any substance that accepts electrons from phenanthrenequinone and/or a derivative thereof and whose optical characteristics change as a result of reduction can be used as the second mediator.

WORKING EXAMPLES

1. Solubility of Mediator

The results of using 9,10-phenanthrenequinone ((d) in the above formula) and sodium 9,10-phenanthrenequinone-2-sulfonate ((i) in the following formula) solubility as an example, and comparing the solubility with that of potassium ferricyanide will now be discussed.

[Third Chemical Formula]

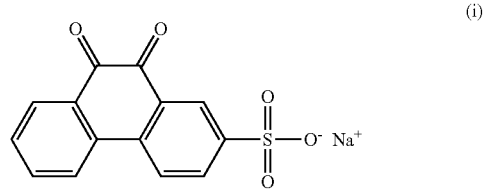

A commercially available 9,10-phenanthrenequinone was sulfonylated with fuming sulfuric acid, after which isomer sorting was performed, and then the product was made into a sodium salt to obtain sodium 9,10-phenanthrenequinone-2-sulfonate. The reaction formula is given below.

[Fourth Chemical Formula]

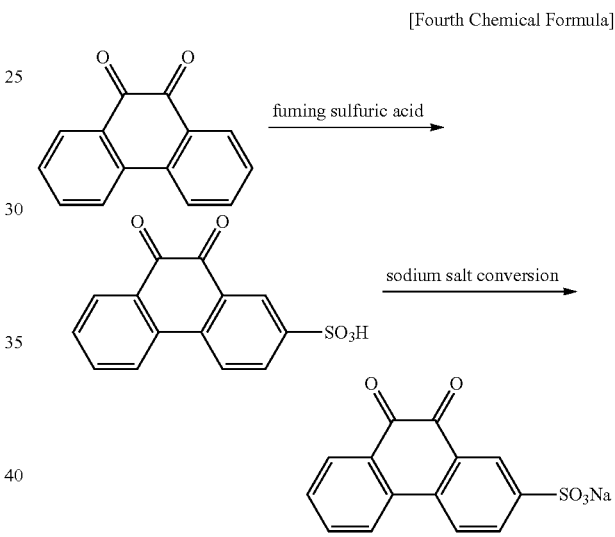

Potassium ferricyanide, 9,10-phenanthrenequinone, and sodium 9,10-phenanthrene-quinone-2-sulfonate were weighed out, and water was added to them. The solubility in water at 25° C. was evaluated visually. The results are given in Table 1.

TABLE 1

| Mediator | Solubility in water |
|---|---|
| potassium ferricyanide | over 100 mM |
| 9,10-phenanthrenequinone | less than 1 mM |
| sodium 9,10-phenanthrenequinone-2-sulfonate | over 80 mM |

As shown in Table 1, the sodium 9,10-phenanthrenequinone-2-sulfonate exhibits good solubility as a mediator in a sensor used for a liquid sample in which water is the solvent.

2. Redox Potential

Potassium ferricyanide and sodium 9,10-phenanthrenequinone-2-sulfonate were each dissolved in an amount of 1 mM in a 100 mM phosphate buffer (pH 7), to prepare a potassium ferricyanide aqueous solution and a sodium 9,10-phenanthrenequinone-2-sulfonate aqueous solution.

These aqueous solutions were used to measure the redox potential by cyclic voltammetry for potassium ferricyanide and sodium 9,10-phenanthrenequinone-2-sulfonate. More specifically, the electrodes used here were as follows.

working electrode: glassy carbon electrode
counter electrode: platinum wire
reference electrode: silver/silver chloride (saturated potassium chloride) electrode (hereinafter referred to as Ag|AgCl).

A potentiostat was used for measurement. The various electrodes and the potentiostat were types commonly used in electrochemistry. This equipment can be purchased from BAS, for example.

The cyclic voltammetry involved searching for the potential applied to the working electrode, linearly with respect to time. The sweep rate was set to 0.1 V/second. First, a first potential was applied to the working electrode, and the electrode potential was swept to the negative side from the starting potential to a second potential that was more negative. Then, sweep was performed in which the electrode potential was flipped back to the positive side from the second potential to the first potential.

The first and second potentials were 0.7 V and −0.3 V, respectively, in the case of potassium ferricyanide, and were 0.2 V and −0.5 V in the case of sodium 9,10-phenanthrene-quinone-2-sulfonate.

The potential discussed next is the potential with respect to Ag|AgCl.

Figure 4:
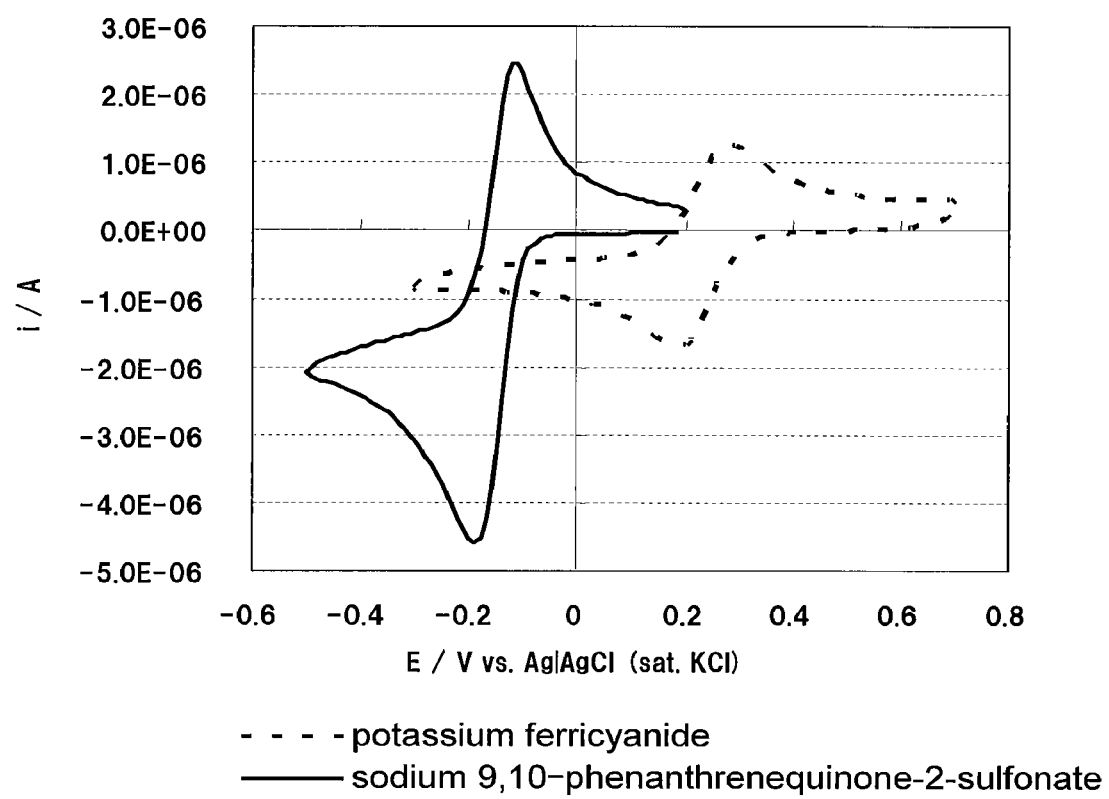
FIG. 4 is a cyclic voltammogram of sodium 9,10-phenanthrenequinone-2-sulfonate (solid line) and a cyclic voltammogram of potassium ferricyanide (dotted line)

The results are given in FIG. 4. For potassium ferricyanide, the potential was 280 mV at the peak oxidation current, and the potential was 170 mV at the peak reduction current. In contrast, for sodium 9,10-phenanthrenequinone-2-sulfonate, the potential was −120 mV at the peak oxidation current, and the potential was −180 mV at the peak reduction current.

If we calculate the redox potential as the average value $[(E_{red}+E_{ox})/2]$ of the potential value at the peak oxidation current ($E_{ox}$) and the potential value at the peak reduction current ($E_{red}$), the redox potential for the sodium 9,10-phenanthrenequinone-2-sulfonate is −150 mV and the redox potential for potassium ferricyanide is 225 mV. Thus, the redox potential for sodium 9,10-phenanthrenequinone-2-sulfonate measured using Ag|AgCl as a reference electrode was negative.

Sodium 9,10-phenanthrenequinone-2-sulfonate undergoes a redox reaction quickly and reversibly with a glassy carbon electrode, and at the same time, has a redox potential that is about 400 mV lower than that of potassium ferricyanide. Being able to react quickly and reversibly with the electrode is a favorable characteristic for a mediator used in a sensor that needs to perform measurement in a short time.

Also, because a substance having a lower redox potential is used as a mediator, the effects of measurement interfering substances that are readily oxidizable in a liquid sample, such as acetaminophen or ascorbic acid in the blood, can be reduced, and as a result a sensor capable of more accurate measurement can be obtained.

3. Glucose Reactivity

With the sensor 1 in the first embodiment, a sensor was produced in which the various components had the following constitution. This is described in further detail below.

First, palladium was sputtered over the substrate 2, which was 30 mm long, 7 mm wide, and 0.2 mm thick and had polyethylene terephthalate as its main component. This formed the conductive layer 3 in a thickness of 8 nm. After this, a non-conductive track with a width of 0.1 mm was formed by laser ablation, which formed the electrodes 31 to 33. The electrode 31 was designed to function as a working electrode, the electrode 32 as a counter electrode, and the electrode 33 as a detecting electrode. Then, a coating of an aqueous solution containing an enzyme and a mediator was applied in a circular shape with a diameter of 2.2 mm using a microsyringe, thereby forming the reagent layer 4. After the reagent layer 4 was formed, the spacer 5 (0.145 mm thick) having a cut-out with a width of 1.2 mm and a length of 3.4 mm and the cover 6 were affixed in that order to the substrate on which the electrodes had been formed, thus producing the sensor 1 equipped with a cavity having a volume of 0.6 µL.

Working Example 1

Sensor Configuration electrode: palladium
reagent layer: The reagent layer was formed by dropping 1.2 µL of an aqueous solution having the following composition (reagent solution) onto the substrate on which the electrodes had been formed, and then drying.
  enzyme: FAD-dependent glucose dehydrogenase 3.5 MU/L (liter)
  mediator: sodium 9,10-phenanthrenequinone-2-sulfonate 0.6 wt % (20 mM)

Comparative Example 1

Sensor Configuration electrode: palladium
reagent layer: The reagent layer was formed by dropping an aqueous solution (1.44) having the following composition onto the substrate on which the electrodes had been formed, and then drying.
  enzyme: FAD-dependent glucose dehydrogenase 1.4 MU/L (liter)
  mediator: potassium ferricyanide 1.7 wt % (52 mM)

Using the sensors of Working Example 1 and Comparative Example 2, glucose concentration measurement was performed by the measurement system 100, using blood with various glucose concentrations (known) as the liquid sample.

Figure 5:
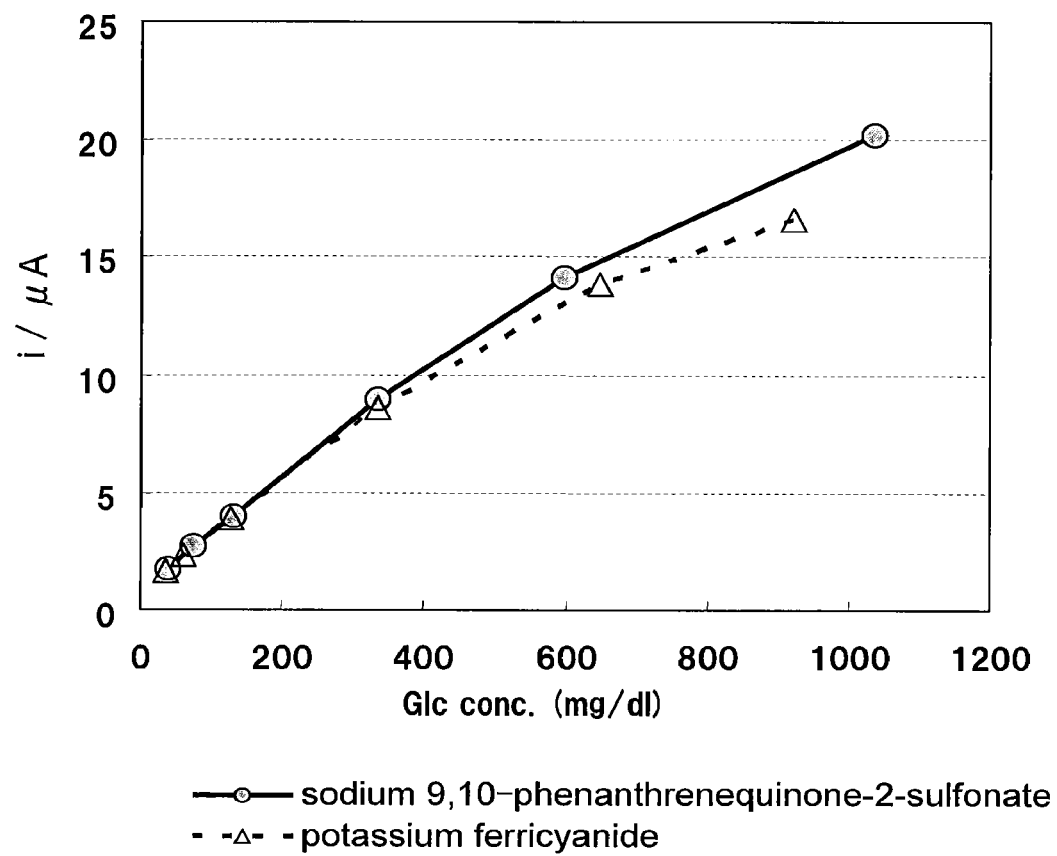
FIG. 5 is a graph of the relation between glucose concentration and the response current of a sensor that makes use of sodium 9,10-phenanthrenequinone-2-sulfonate (solid line) and of a sensor that makes use of potassium ferricyanide (dotted line)

The results are given in FIG. 5. The sensor having sodium 9,10-phenanthrene-quinone-2-sulfonate exhibited equal or better glucose response compared to the sensor having potassium ferricyanide.

4. Reproducibility

Using the sensors from section 3. above, the reproducibility of the glucose concentration measurement results was examined. Using blood with various glucose concentrations (known) as the liquid sample, and measuring with six to ten sensors at the same time, the average value and standard deviation were calculated, and the standard deviation was divided by the average value to evaluate the simultaneous reproducibility.

Figure 6:
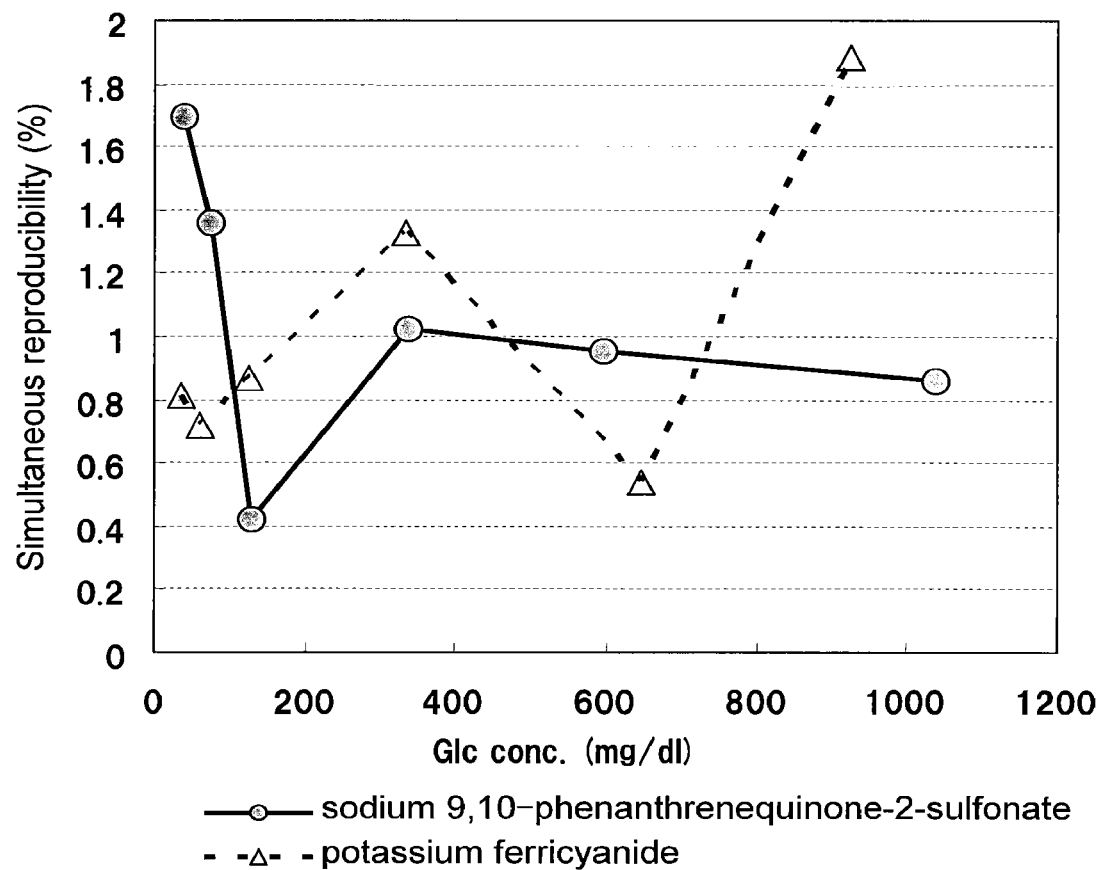
FIG. 6 is a graph of the relation between glucose concentration and the simultaneous reproducibility of glucose concentration measurement with a sensor that makes use of sodium 9,10-phenanthrenequinone-2-sulfonate (solid line) and with a sensor that makes use of potassium ferricyanide (dotted line)

FIG. 6 shows the results of plotting glucose concentration on the horizontal axis and simultaneous reproducibility on the vertical axis (the quotient of dividing the standard deviation by the average measured value). The sensor having the sodium 9,10-phenanthrene-quinone-2-sulfonate exhibited equal or better reproducibility as compared to the sensor having the potassium ferricyanide.

5. Effect of Interfering Substances

The effect of interfering substances was examined using the sensors in section 3. above.

Figure 7:
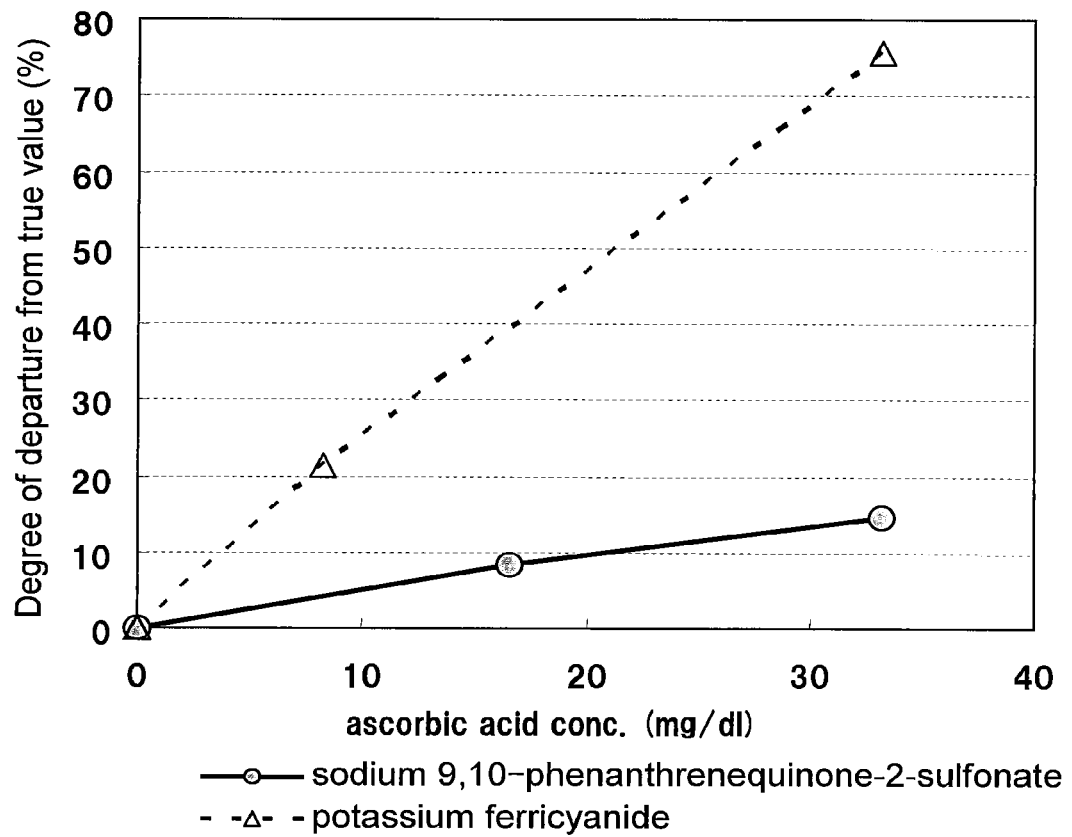
FIG. 7 is a graph of the relation between ascorbic acid concentration and the degree of departure from the true value of the glucose concentration measurement result obtained with a sensor that makes use of sodium 9,10-phenanthrenequinone-2-sulfonate (solid line) and with a sensor that makes use of potassium ferricyanide (dotted line)

The sensors were used to measure the glucose concentration, using blood to which interfering substances had been added in various concentrations as the liquid sample (glucose concentration of 80 mg/dL). The degree of departure (%) from the true value was found for the average value of six to ten measurements. FIG. 7 shows the results when ascorbic acid was used as an interfering substance, and FIG. 8 shows the results when acetaminophen was used as an interfering substance.

Figure 8:
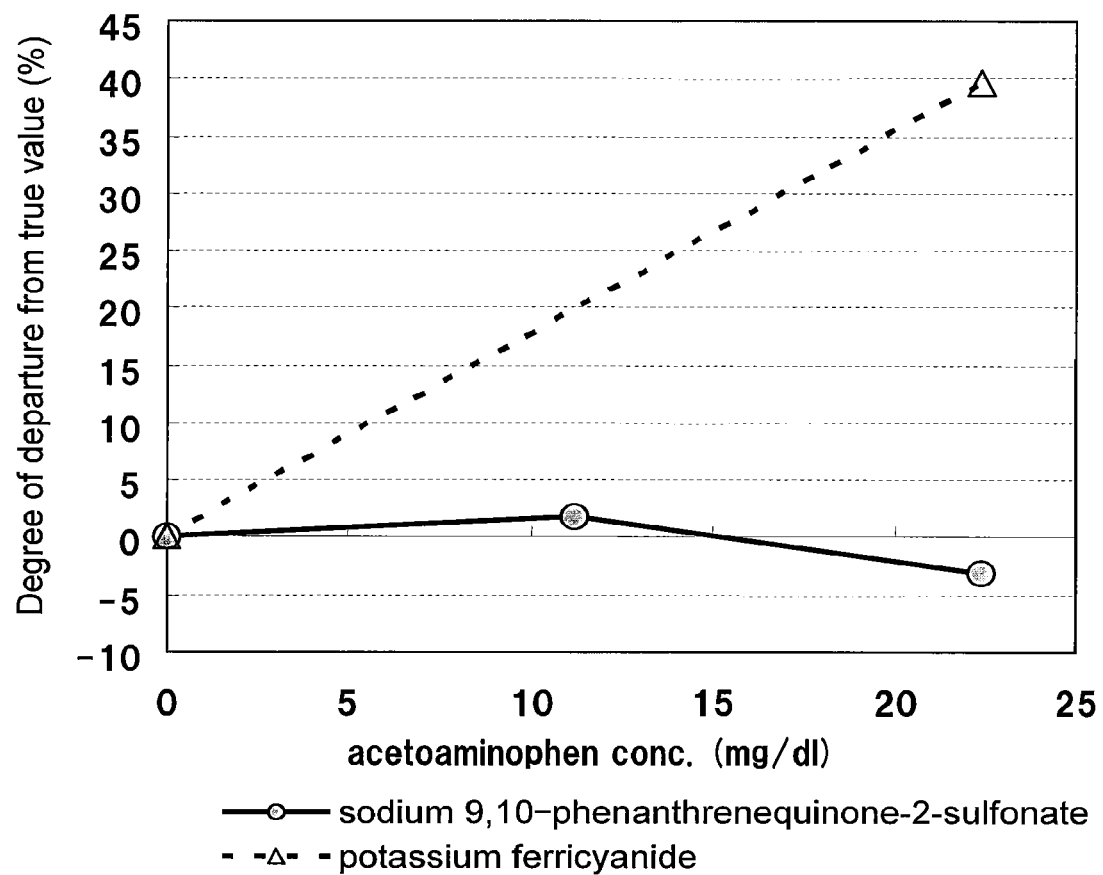
FIG. 8 is a graph of the relation between acetaminophen concentration and the degree of departure from the true value of the glucose concentration measurement result obtained with a sensor that makes use of sodium 9,10-phenanthrenequinone-2-sulfonate (solid line) and with a sensor that makes use of potassium ferricyanide (dotted line)

As shown in FIGS. 7 and 8, with the sensor having the sodium 9,10-phenanthrenequinone-2-sulfonate, the effect of the interfering substances was reduced more than with the sensor having potassium ferricyanide. This seems to be attributable to the fact that the sodium 9,10-phenanthrenequinone-2-sulfonate used as a mediator has a lower redox potential than potassium ferricyanide.

Figure 9:
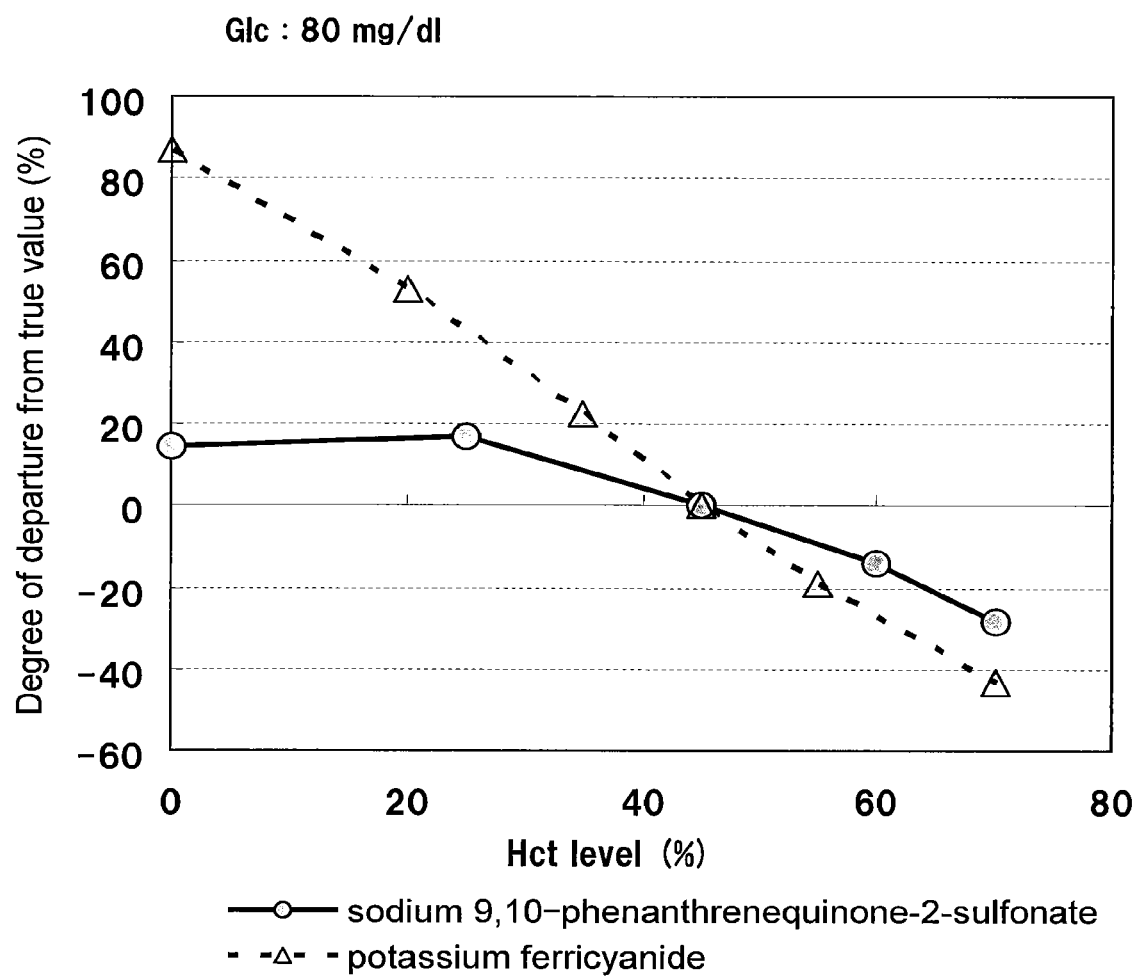
FIG. 9 is a graph of the relation between the hematocrit level and the degree of departure from the true value of the glucose concentration measurement result obtained with a sensor that makes use of sodium 9,10-phenanthrenequinone-2-sulfonate (solid line) and with a sensor that makes use of potassium ferricyanide (dotted line), at a glucose concentration of 80 mg/dL.
Figure 10:
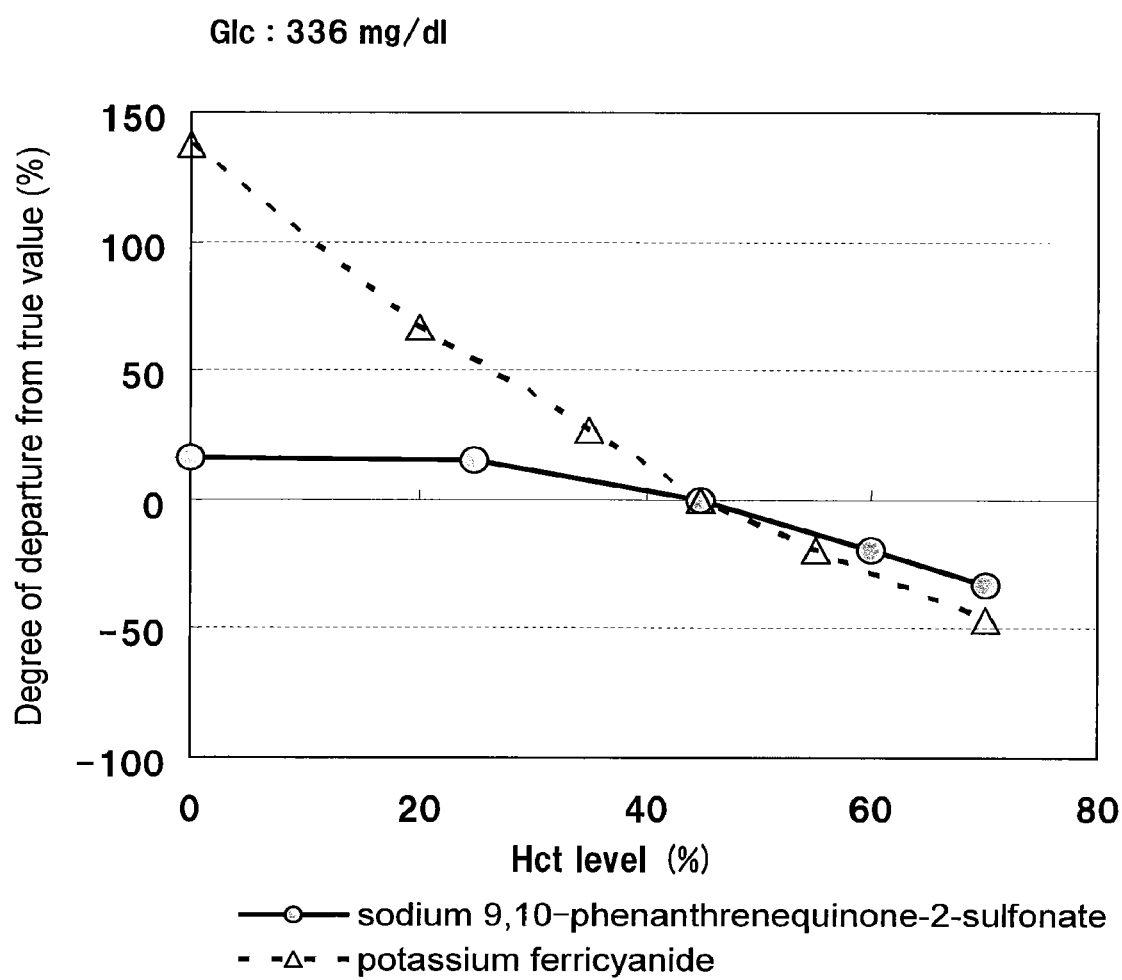
FIG. 10 is a graph of the relation between the hematocrit level and the degree of departure from the true value of the glucose concentration measurement result obtained with a sensor that makes use of sodium 9,10-phenanthrenequinone-2-sulfonate (solid line) and with a sensor that makes use of potassium ferricyanide (dotted line), at a glucose concentration of 336 mg/dL.

FIGS. 9 and 10 show the degree of departure from the true value of the measured glucose concentration at hematocrit levels of 0% to 70%. In FIG. 9 the glucose concentration is 80 mg/dL, and in FIG. 10 the glucose concentration is 336 mg/dL.

As shown in FIGS. 9 and 10, the effect of hematocrit was reduced more with the sensor having sodium 9,10-phenanthrenequinone-2-sulfonate than with the sensor having potassium ferricyanide.

6. Other Mediators

As shown in FIG. 11, compounds A, B, H', I, I', and J were synthesized using 9,10-phenanthrenequinone as the starting substance. p-TsOH in FIG. 11 stands for p-toluenesulfonic acid.

Table 2 shows the solubility of compounds A, B, H', I, I', and J and disodium 9,10-phenanthrenequinone-2,7-disulfonate in water.

TABLE 2

| Mediator | Solubility in water |
| --- | --- |
| disodium 9,10-phenanthrenequinone-2,7-disulfonate | over 200 mM |
| compound A | 1 mM |
| compound B | 1 mM |
| compound H' | 20 mM |
| compound I | 5 mM |
| compound I' | 20 mM |
| compound J | 50 mM |

Compounds H', I, I', and J and disodium 9,10-phenanthrenequinone-2,7-disulfonate have a hydrophilic functional group, and as shown in Table 2, exhibited high solubility in water.

The compounds having a hydrophilic functional group, namely, disodium 9,10-phenanthrenequinone-2,7-disulfonate and compounds H', I, I', and J, exhibited particularly high solubility.

Figure 12:
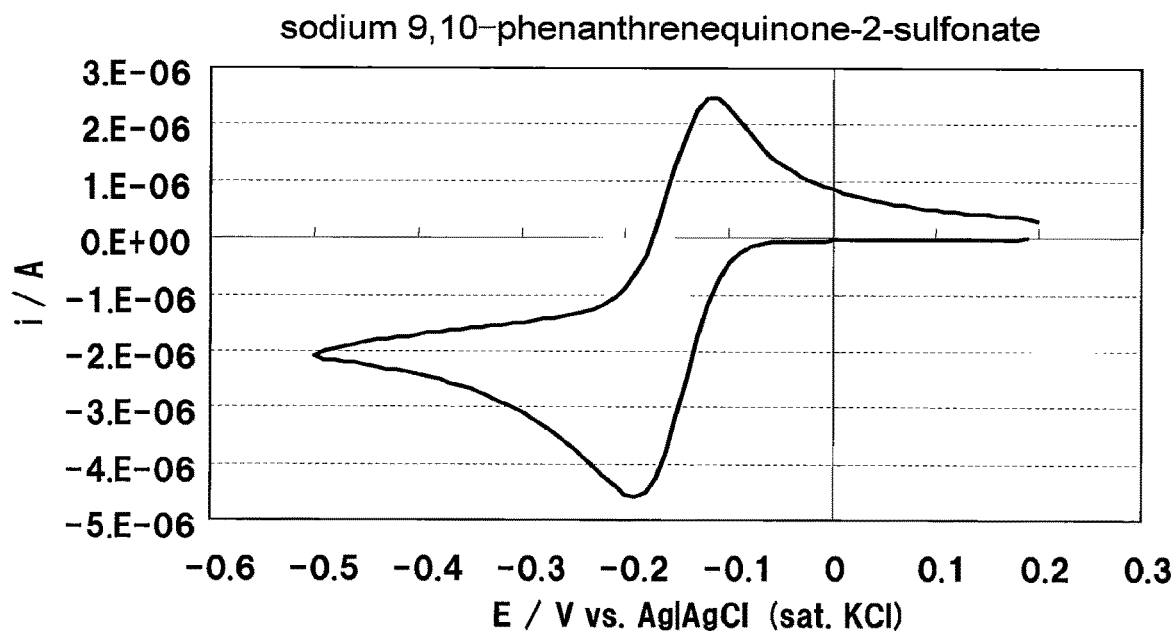
FIG. 12 is a cyclic voltammogram of sodium 9,10-phenanthrenequinone-2-sulfonate.
Figure 13:
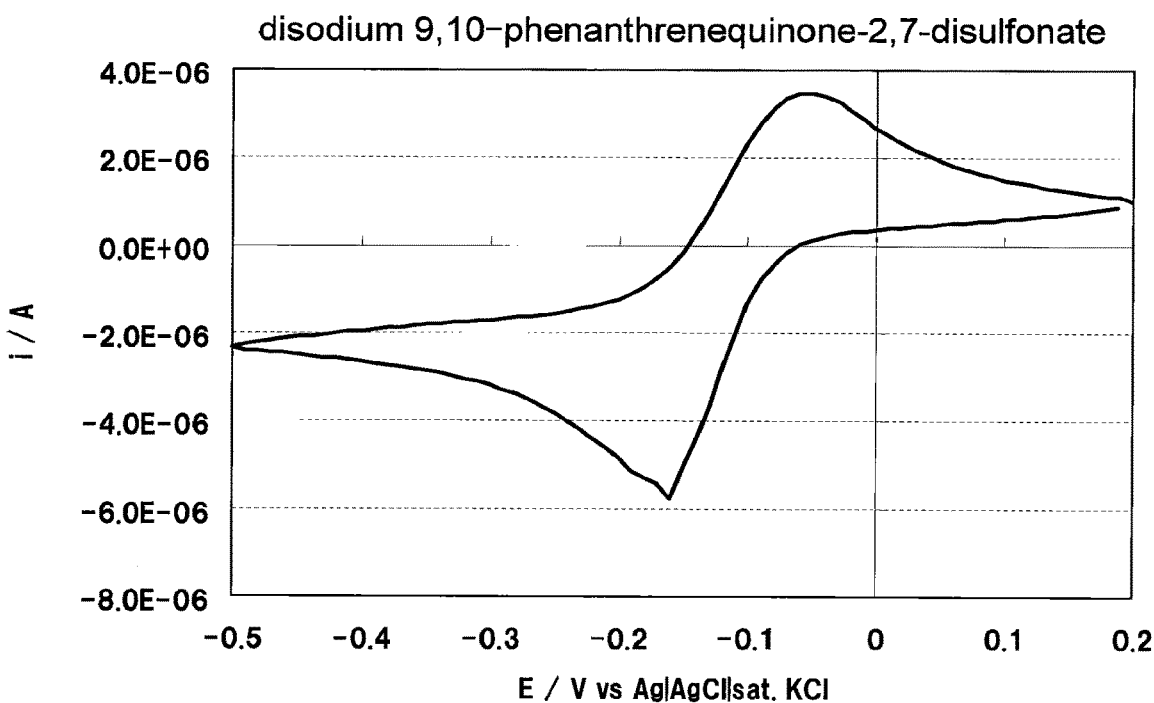
FIG. 13 is a cyclic voltammogram of disodium 9,10-phenanthrenequinone-2,7-disulfonate.
Figure 14:
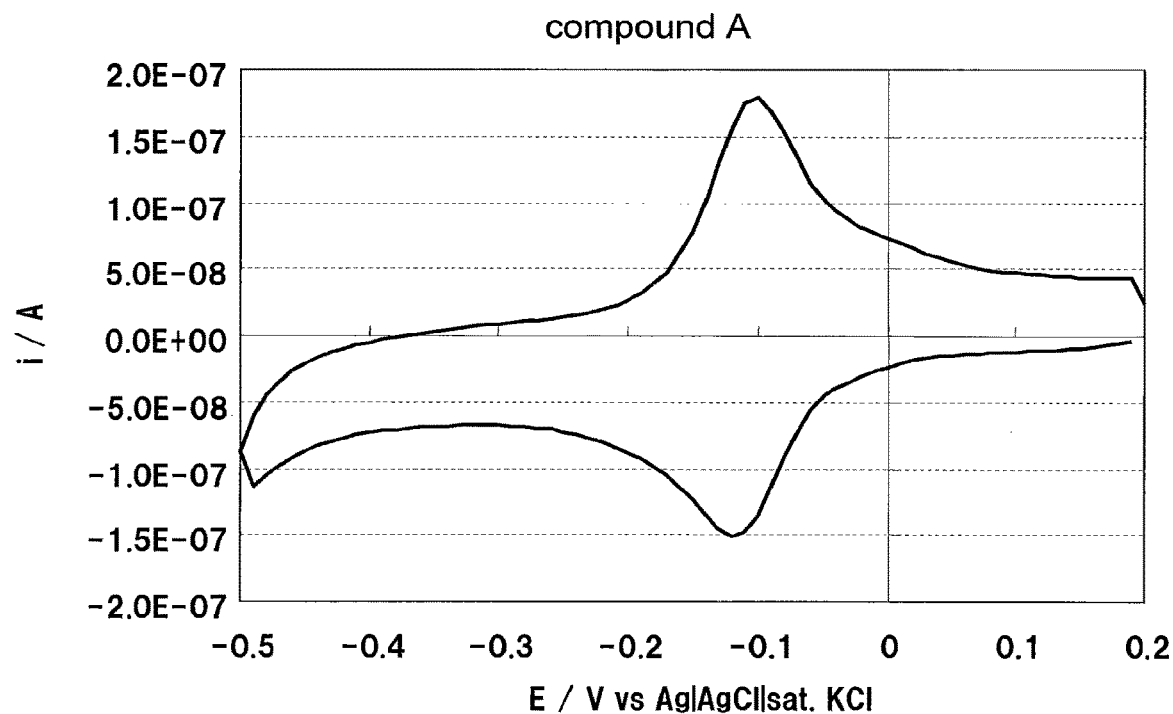
FIG. 14 is a cyclic voltammogram of a compound A.
Figure 15:
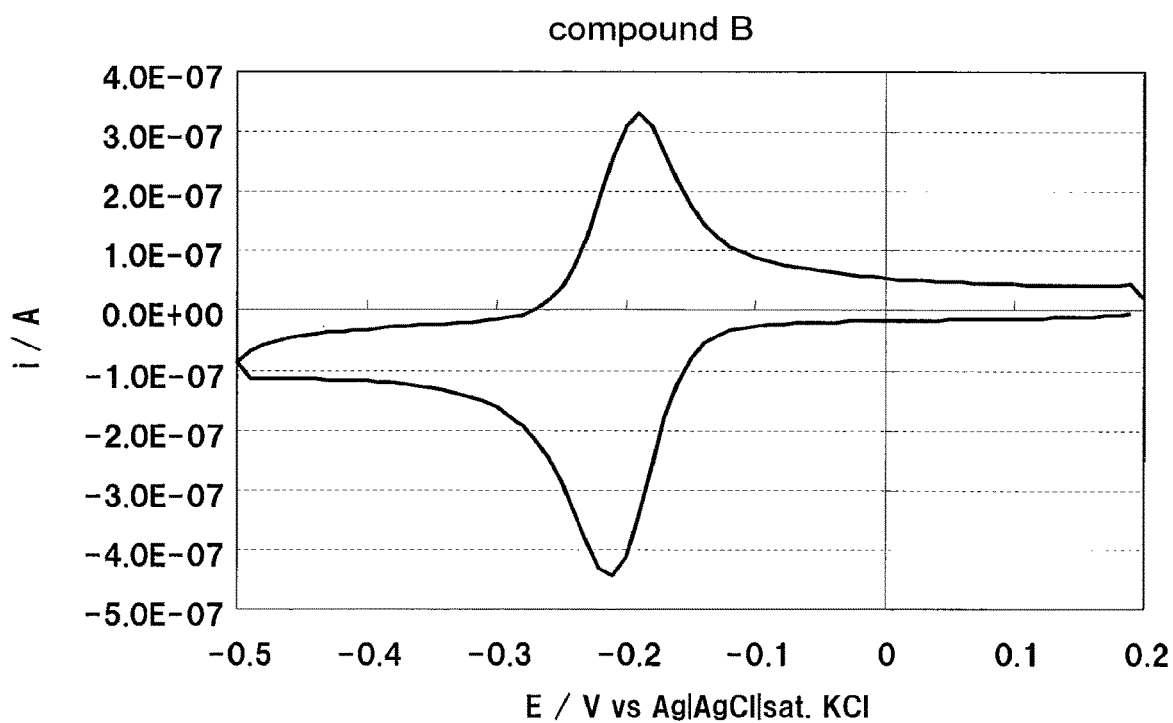
FIG. 15 is a cyclic voltammogram of a compound B.
Figure 16:
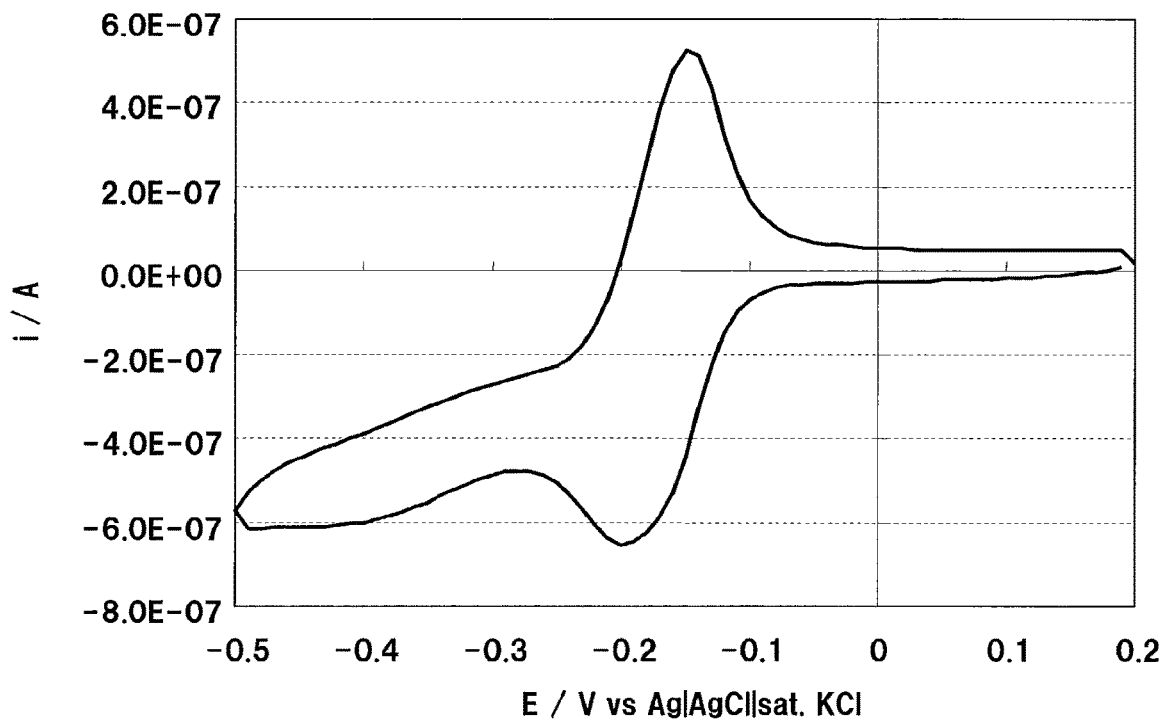
FIG. 16 is a cyclic voltammogram of a compound H.
Figure 17:
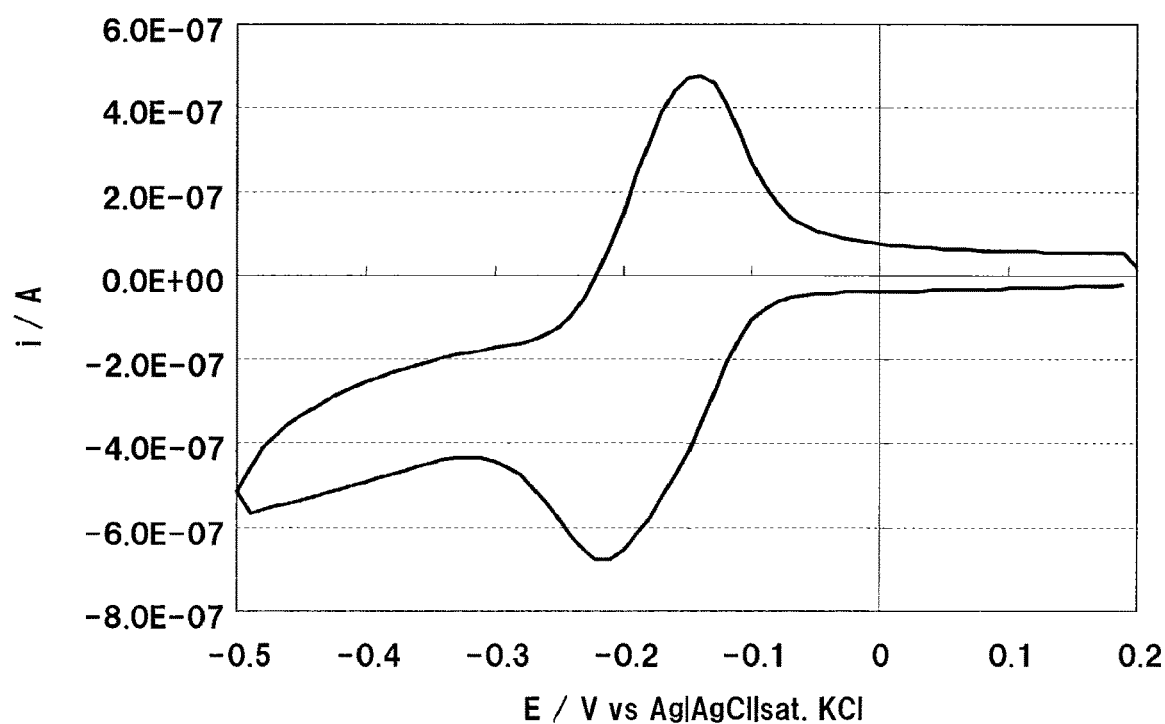
FIG. 17 is a cyclic voltammogram of a compound I.
Figure 18:
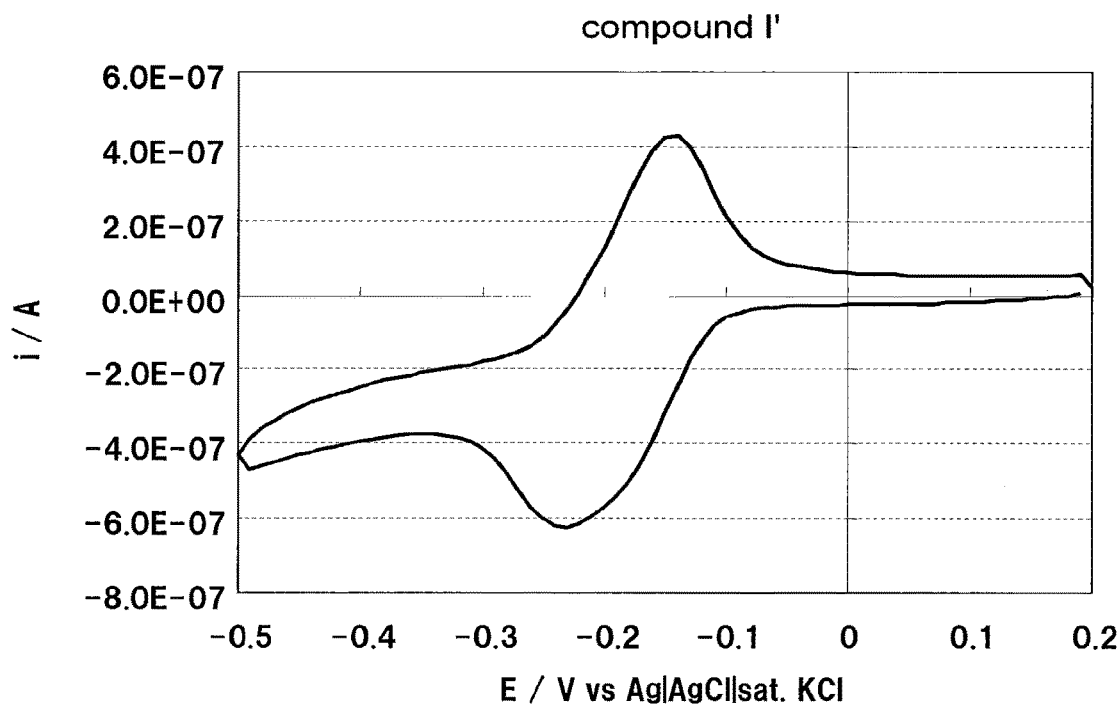
FIG. 18 is a cyclic voltammogram of a compound I.
Figure 19:
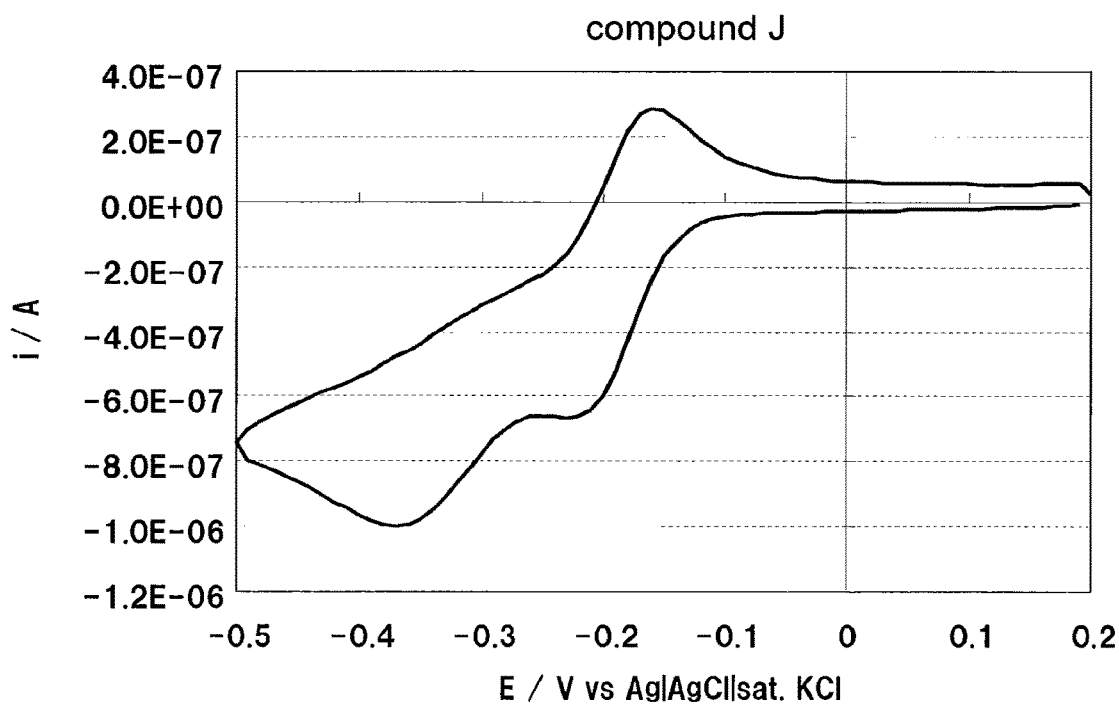
FIG. 19 is a cyclic voltammogram of a compound J.

Also, compounds A, B, H', I, I', and J and disodium 9,10-phenanthrenequinone-2,7-disulfonate were subjected to cyclic voltammetry by the same operation as in FIG. 4. The cyclic voltammograms are shown in FIGS. 13 to 19. For the sake of comparison, FIG. 12 shows a cyclic voltammogram for the sodium 9,10-phenanthrenequinone-2-sulfonate in FIG. 4. Table 3 shows the potential value at the peak reduction current ($E_{red}$), the potential value at the peak oxidation current ($E_{ox}$), and the redox potential (E0').

TABLE 3

| Mediator | $E_{red}$ (V) | $E_{ox}$ (V) | E0' (V) [($E_{red}$ + $E_{ox}$)/2] |
| --- | --- | --- | --- |
| sodium 9,10-phenanthrenequinone-2-sulfonate | −0.18 | −0.12 | −0.15 |
| disodium 9,10-phenanthrenequinone-2,7-disulfonate | −0.18 | −0.06 | −0.12 |
| compound A | −0.13 | −0.10 | −0.12 |
| compound B | −0.23 | −0.19 | −0.21 |
| compound H' | −0.21 | −0.14 | −0.18 |
| compound I | −0.22 | −0.14 | −0.18 |
| compound I' | −0.22 | −0.14 | −0.18 |
| compound J | −0.23 | −0.15 | −0.19 |

As shown in Table 3, the redox potential of these compounds, measured using Ag|AgCl as a reference electrode, was negative.

7. Effect of Buffer

An N-(2-acetamide)-2-aminoethanesulfonic acid (ACES) buffer (pH 7.0) was used as a solvent for a reagent solution used to form a reagent layer. The other conditions (such as the types and concentrations of enzyme and mediator in the reagent solution) were the same as in Working Example 1. The response current value corresponding to the glucose concentration was measured for when the buffer section (ACES) concentration was 0, 10, 20, and 30 mM. The results are shown in FIG. 20.

Figure 20:
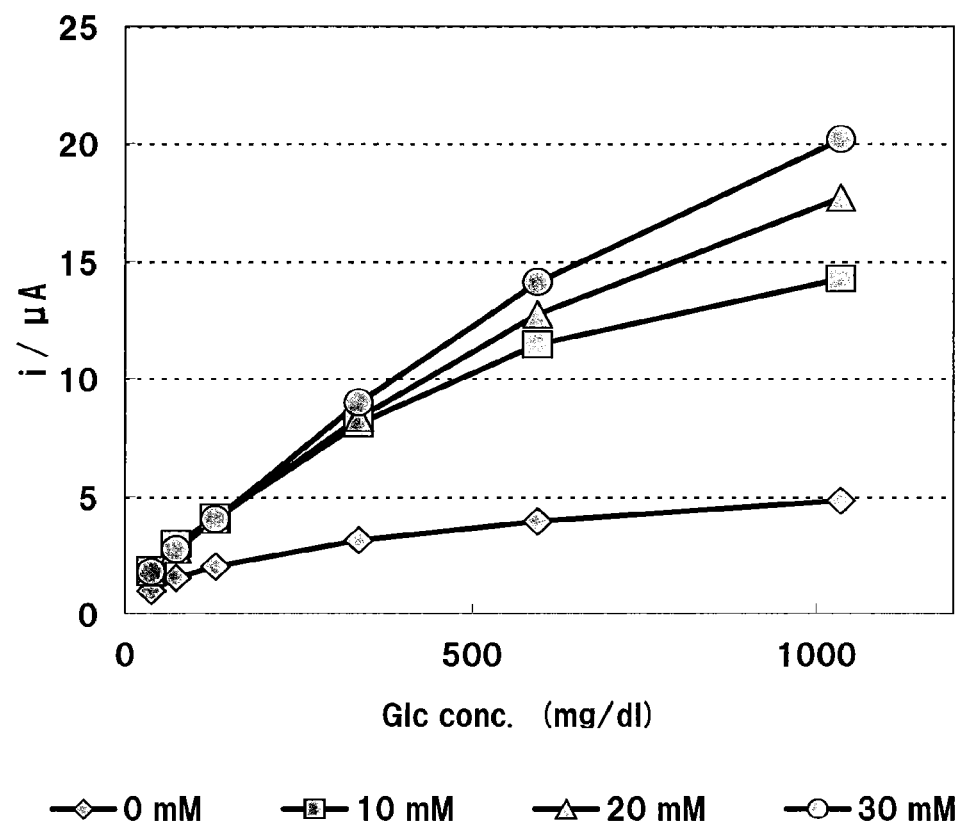
FIG. 20 is a graph of the increase in the response of a sensor due to a buffer section in a reagent solution that forms a reagent layer.

As shown in FIG. 20, the response of the sensor with respect to the glucose concentration improves with the presence of ACES. Also, better response was obtained at a higher ACES concentration.

The inventors also used a phosphate buffer instead of an ACES buffer to confirm an improvement in the response of a sensor with respect to glucose concentration.

8. pH of Reagent Solution

Three kinds of reagent were prepared by using phosphate buffers with a pH of 6.4, 7.0, and 7.5 as the solvent. These reagents were used to form a reagent layer and to produce three kinds of sensor. The other conditions were the same as in Working Example 1.

Figure 21:
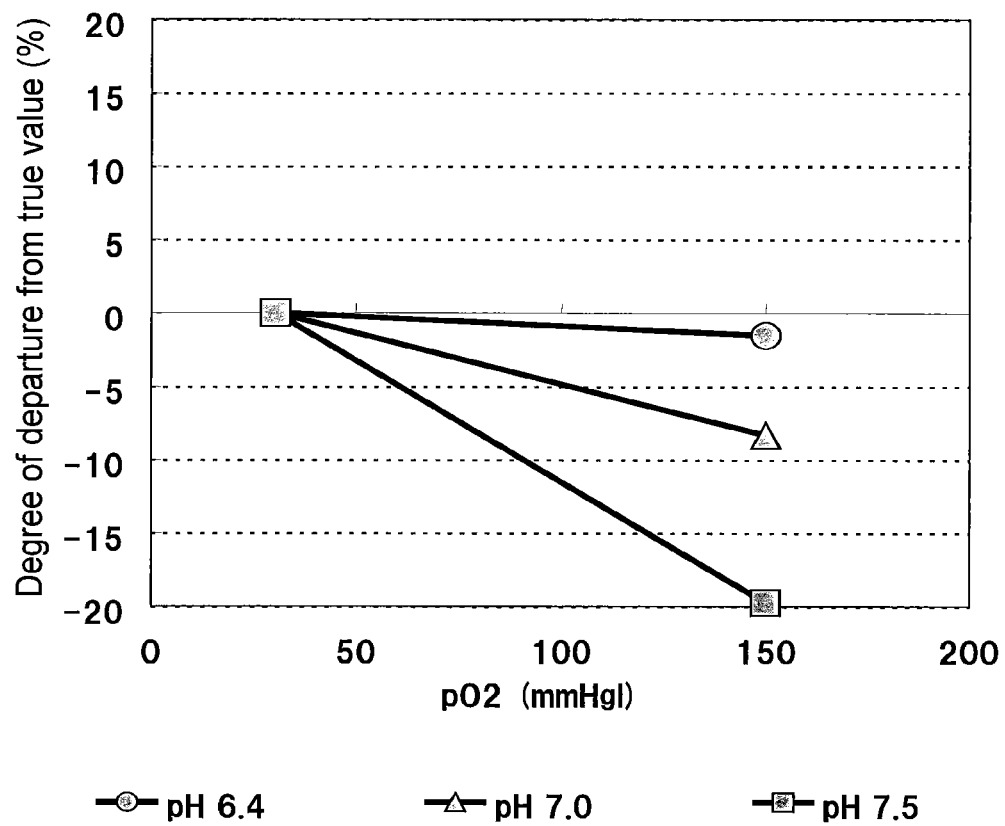
FIG. 21 is a graph of the effect of reducing the influence of dissolved oxygen due to the pH of the reagent solution.

These sensors were used to measure the glucose concentration in blood. As shown in FIG. 21, an oxygen dissolved in the blood affects the glucose concentration measurement result. However, the effect of the oxygen was reduced by using a buffer with a pH of 7.0, as compared to when a buffer with a pH of 7.5 was used. This effect was reduced even further when a buffer with a pH of 6.4 was used.

9. Additives

A reagent was prepared using a phosphate buffer with a pH of 6.4 as a solvent, and this reagent was used to form a reagent layer. The response current of the sensor with respect to the glucose concentration was compared between when 10 mM trisodium citrate was added to the reagent, and when it was not added. Other than using a phosphate buffer with a pH of 6.4 as a solvent and adding trisodium citrate, the conditions were the same as in Working Example 1.

Figure 22:
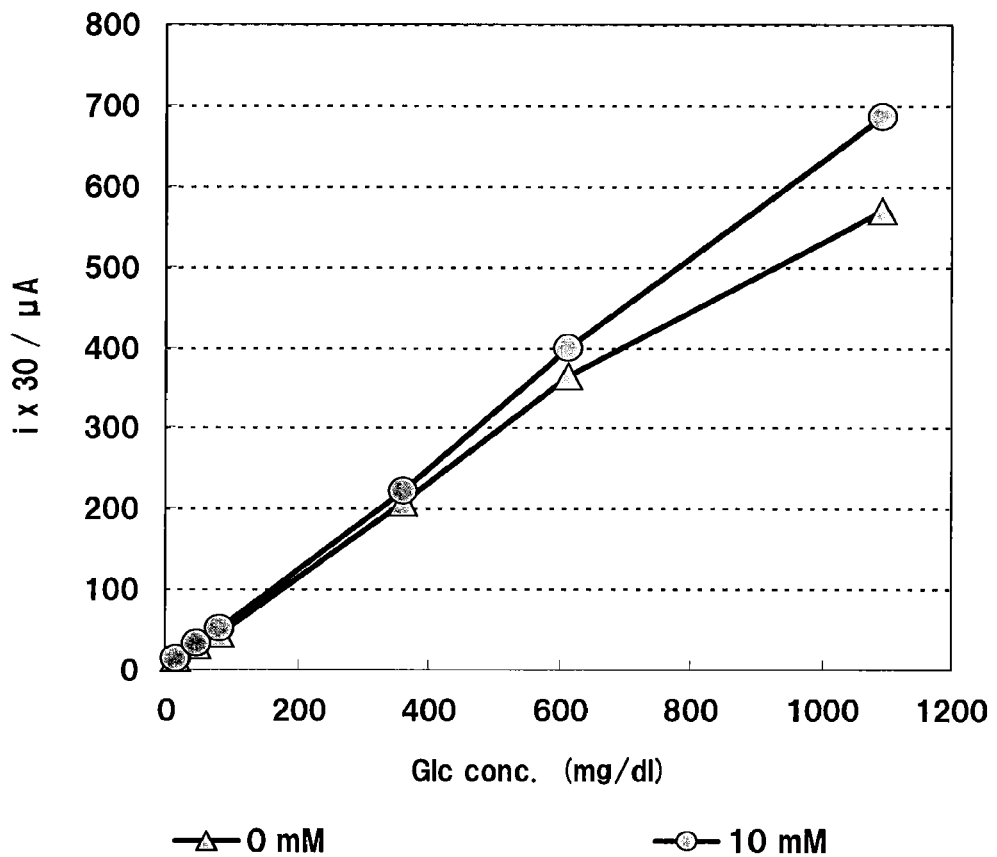
FIG. 22 is a graph of the increase in the response of a sensor due to trisodium citrate in a reagent solution.

As shown in FIG. 22, adding trisodium citrate improved the linearity of the response current with respect to the glucose concentration.

Also, a similar effect was noted when calcium chloride ($CaCl_2$) was used in place of trisodium citrate.

REFERENCE SIGNS LIST 1 sensor
2 substrate
3 conductive layer
31 working electrode
32 counter electrode
33 detecting electrode
4 reagent layer
5 spacer
51 capillary
52 inlet
6 cover
61 vent hole

The invention claimed is:

1. A sensor for detecting or quantifying a target substance contained in a liquid sample including blood, comprising:
   a working electrode;
   a counter electrode;
   a quinone compound having quinone and at least one hydrophilic substituent;
   a coenzyme-dependent enzyme dehydrogenating or oxidizing the target substance; and
   a reagent layer including the coenzyme-dependent enzyme and the quinone compound,
   wherein the reagent layer is disposed so as to be in direct physical contact with the working electrode and/or the counter electrode,
   the oxidation-reduction potential of the quinone compound measured using a silver/silver chloride (saturated potassium chloride) electrode as a reference electrode is less than 0, is greater than oxidation reduction potential of the coenzyme, and is smaller than oxidation reduction potential of ascorbic acid,
   the hydrophilic substituent has a benzene ring and a hydrophilic functional group added to the benzene ring,
   the coenzyme-dependent enzyme is a PQQ-dependent, an FAD-dependent, or an NAD-dependent enzyme, and
   the quinone is a phenanthrenequinone.

2. The sensor according to any of claim 1,
   wherein the substituent has at least one type of functional group selected from the group consisting of a sulfonic acid group, a carboxylic acid group, and a phosphoric acid group.

3. The sensor according to claim 1,
   wherein the phenanthrenequinone is a 9,10-phenanthrenequinone.

4. The sensor according to claim 1, wherein the reagent layer is dissolved into the liquid sample.

5. The sensor according to claim 1, wherein a solubility of the phenanthrenequinone derivative in water is 80 mM or more.

* * * * *